(12) United States Patent
Biesinger et al.

(10) Patent No.: US 9,138,274 B1
(45) Date of Patent: Sep. 22, 2015

(54) FASTENERS WITH SHAPE CHANGING BELLOWS AND METHODS USING SAME

(75) Inventors: David P. Biesinger, Las Vegas, NV (US); James A. Biesinger, Bethesda, MD (US)

(73) Assignee: Xtraverse, LLC, Las Vegas, NV (US)

( * ) Notice: Subject to any disclaimer, the term of this patent is extended or adjusted under 35 U.S.C. 154(b) by 230 days.

(21) Appl. No.: 13/463,987

(22) Filed: May 4, 2012

(51) Int. Cl.
| | | |
|---|---|---|
| A61B 17/84 | (2006.01) | |
| A61B 17/56 | (2006.01) | |
| A61B 17/86 | (2006.01) | |

(52) U.S. Cl.
CPC .............. *A61B 17/844* (2013.01); *A61B 17/864* (2013.01); *A61B 17/866* (2013.01); *A61B 17/8685* (2013.01); *A61B 2017/564* (2013.01)

(58) Field of Classification Search
CPC ........ A61B 17/00; A61B 17/56; A61B 17/58; A61B 17/60; A61B 17/064; A61B 17/04; A61B 17/84; A61B 17/86; A61B 17/66; A61B 17/864; A61B 17/8685; A61F 2/30; A61F 2/00; A61F 2/46; A61F 2/08; A61F 2/32; A61F 2/44; A61F 5/04; F16B 35/02; F16B 35/00; F16L 51/02
USPC .................. 606/57, 105, 104, 53, 60, 62, 65, 606/72–73, 75, 300, 301, 304, 309–310, 606/316, 318–321, 326, 328–329, 282, 232, 606/213; 623/21, 22.16, 21.11, 21.15, 623/23.44, 22, 21.12–21.19, 17.11, 17.13, 623/17.15, 17.16; 411/383, 389, 392; 285/226–227; 138/121
See application file for complete search history.

(56) References Cited

U.S. PATENT DOCUMENTS

| | | | |
|---|---|---|---|
| 4,719,917 A * | 1/1988 | Barrows et al. | 606/220 |
| 5,246,443 A | 9/1993 | Mai | |
| 5,263,973 A * | 11/1993 | Cook | 606/216 |
| 5,282,829 A * | 2/1994 | Hermes | 606/219 |
| 5,417,692 A | 5/1995 | Goble et al. | |
| 5,919,193 A | 7/1999 | Slavitt | |
| 6,059,787 A * | 5/2000 | Allen | 606/75 |
| 7,041,106 B1 | 5/2006 | Carver et al. | |
| 7,819,877 B2 | 10/2010 | Guzman et al. | |
| 7,942,875 B2 | 5/2011 | Nelson et al. | |
| 7,985,231 B2 | 7/2011 | Sankaran | |
| 8,152,775 B2 * | 4/2012 | DeSantis et al. | 604/174 |
| 8,454,653 B2 * | 6/2013 | Hadba et al. | 606/228 |
| 2003/0139746 A1 * | 7/2003 | Groiso | 606/75 |
| 2008/0015598 A1 * | 1/2008 | Prommersberger | 606/75 |
| 2008/0065153 A1 * | 3/2008 | Allard et al. | 606/219 |

(Continued)

OTHER PUBLICATIONS

Technique Guide dated Jun. 2009 [see pp. 11-15 (slides 13-17)] http://www.synthes.com/MediaBin/International%20DATA/036.000.266.pdf.

*Primary Examiner* — Todd Manahan
*Assistant Examiner* — Marcela I Shirsat
(74) *Attorney, Agent, or Firm* — Townsend M. Belser, Jr.; Nexsen Pruet, LLC

(57) ABSTRACT

A fastening device having a bellows made of a material that changes shape when activated by a catalyst, and having a pleated structure that contracts from an extended state to a contracted state upon activation. The shape changing material may be a shape memory metal alloy, shape memory polymer or elastic memory composite. A method of using this fastener provides apposition and compression of abutment surfaces to join together two pieces of material, and is suitable for joining apposing bone surfaces together to heal fractures via the use of orthopedic hardware.

20 Claims, 17 Drawing Sheets

(56) References Cited

U.S. PATENT DOCUMENTS

| | | |
|---|---|---|
| 2008/0177262 A1 | 7/2008 | Augoyard et al. |
| 2009/0062799 A1* | 3/2009 | Holsten et al. .......... 606/75 |
| 2009/0210016 A1 | 8/2009 | Champagne |
| 2009/0228048 A1 | 9/2009 | Duncan et al. |
| 2010/0070043 A1 | 3/2010 | Kitchen |
| 2010/0125275 A1* | 5/2010 | Kinmon et al. .......... 606/75 |
| 2010/0131014 A1 | 5/2010 | Peyrot et al. |
| 2011/0004255 A1 | 1/2011 | Weiner et al. |
| 2011/0054545 A1 | 3/2011 | Champagne et al. |
| 2011/0082508 A1 | 4/2011 | Reed |
| 2011/0144645 A1 | 6/2011 | Saravia et al. |
| 2011/0295255 A1* | 12/2011 | Roberts et al. .......... 606/64 |

* cited by examiner

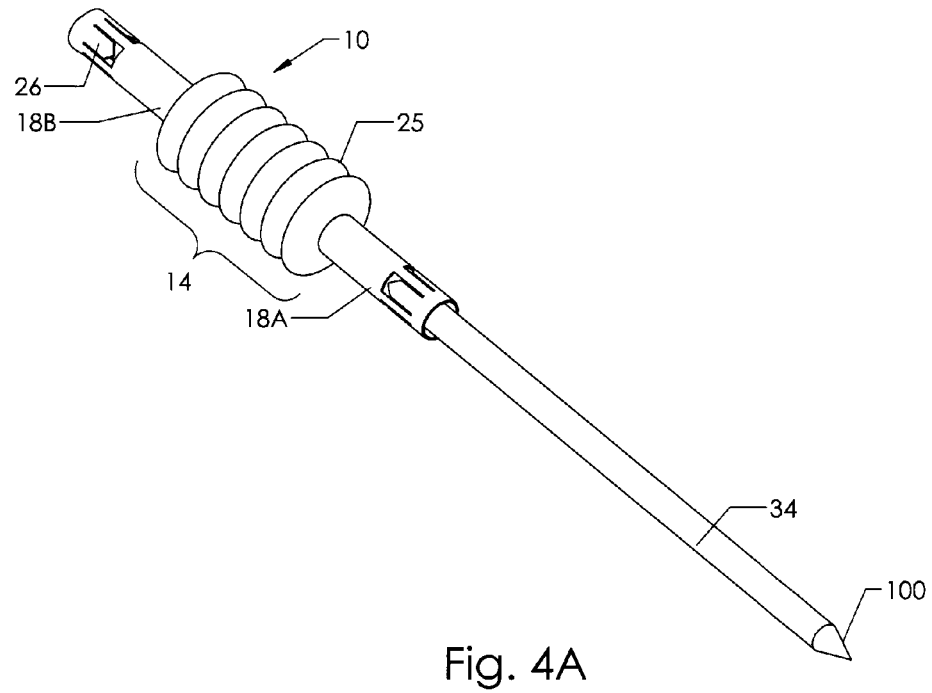
Fig. 4A
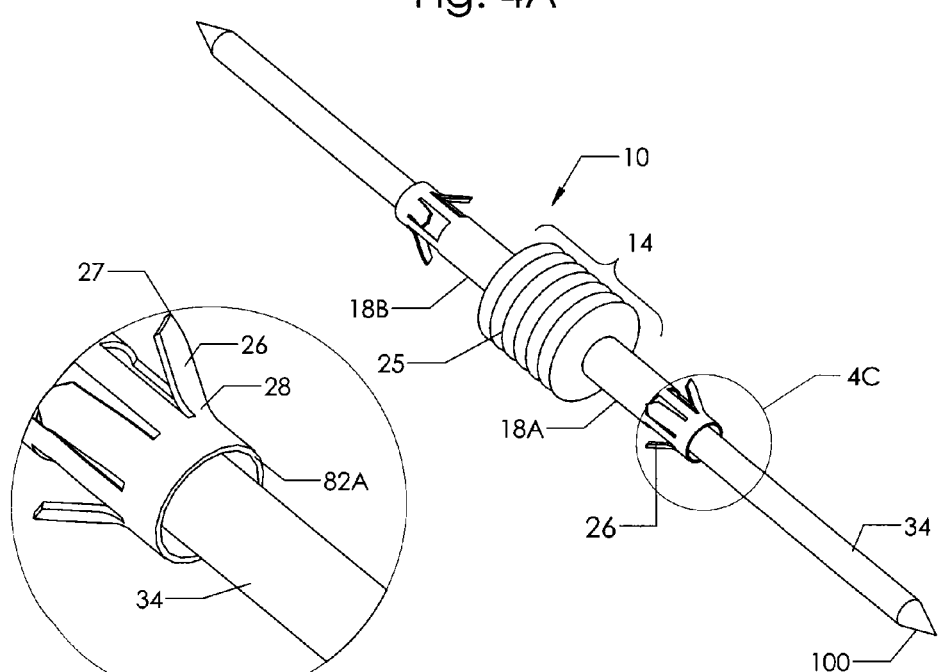
Fig. 4C
Fig. 4B

FASTENERS WITH SHAPE CHANGING BELLOWS AND METHODS USING SAME

TECHNICAL FIELD

The present invention relates generally to the joining and compressing together the surfaces of two or more pieces or parts by utilizing a bellows made from a shape memory material. Anchoring elements at opposite ends of the bellows are inserted into or attached to the respective pieces or parts to be joined together. These could be two or more pieces of wood, plastic, metal, bone, or combinations thereof, though not limited to any of these in particular. More specifically, the present invention has an application in the joining of two bone surfaces together for the purposes of osteosynthesis, or of bone fusion, and it relates particularly to a new and improved orthopedic endoprosthesis for fusing the bones together in a toe or finger.

BACKGROUND OF THE INVENTION

The medical term for a toe or finger is a phalange and any individual bone within a toe or finger is called a phalanx. Deformities of the phalanges are common conditions encountered by surgeons. These deformities can occur for numerous reasons and the deformities have acquired different names such as mallet toe, claw toe, hammertoe, boutonniere deformity, and swan neck deformity, amongst others. Surgeons often address these deformities surgically in an attempt to straighten the phalanges, to alleviate pain, provide stability to the digit, improve ambulation, gait, or dexterity, or prevent further sequelae of phalangeal deformities.

The fixation of bone fractures or surgically manipulated bones with orthopedic hardware such as screws, plates, pins, and staples helps bone to heal. Bone fixation was originally accomplished with externally applied casts or other forms of immobilization which led to high rates of nonunion or malunion as these forms of immobilization afforded little inherent stability at the bone-bone interface. Stability is a critical factor for obtaining consolidation or bone healing. Eventually metallic rods and pins were utilized to increase stability of bone fixation thereby improving healing rates. Eventually further stability was gained through the use of screws across bone and joint surfaces because they added a compressive force across the opposing bone surfaces. Further improvements were made to screws via cannulation which allowed the more rapid placement of the screws, more accuracy, and greater ease of use whether for the repair of fractures or fusing the bones of a joint.

Of particular interest is the fusion of the proximal interphalangeal joint (PIPJ) of the toes and fingers for stabilizing and correcting deformity of these structures. The procedure normally involves resecting or cutting away the joint surfaces of the PIPJ. The two phalanx bones are then placed end to end and a rod or pin is then driven axially along the internal diameter of the phalange providing stability for osteosynthesis. One end of the pin typically remains outside of the skin of the phalange at the tip of the toe or finger during the healing process.

There is concern for many surgeons about the use of pins with this type of surgery because an exposed pin at the distal toe tip may increase the risk of pin tract infections. There is also the possibility of undesired migration of the pins deeper into a bone or the accidental removal of the pin prior to healing of the bone ends. Placing the pin through the skin like this also introduces the pin across the distal interphalangeal joint (DIPJ) and thus violates that joint. Also, the use of pins provides no rotational stability and may allow the phalangeal bones to "piston" on the pin because it is smooth. Therefore some surgeons look toward devices that can be introduced across the PIPJ alone so they do not stick out through the skin, do not violate the DIPJ or the metatarsal phalangeal joint (MTPJ), do not increase the risk for infection, and will provide stability in all planes. However, though there is some legitimacy to these concerns, the use of pins is often necessary when performing toe or finger surgery.

There are times when the surgery for reduction of a toe or finger deformity requires more than just a joint fusion of the PIPJ for proper correction. The release of ligaments and the transfer of tendons are sometimes necessary more proximally at the MTPJ adjacent to the PIPJ or at the DIPJ. This is done at the surgeon's discretion as he or she sees fit and may thus require the use of a pin across one or both of these joints to provide fixation and stability. The DIPJ and MTPJ are rarely fused. Surgeons currently have the option to use a pin and accept its disadvantages, or use some other commercially available product without the use of a pin, each of these having their own disadvantages.

DESCRIPTION OF THE RELATED ART

One particular prior art device allows the placement of an internal fixation device into a PIPJ that does not violate the adjacent MTPJ or DIPJ. The device is comprised of two members that screw into the bone surfaces and are then joined together. One drawback of the device design is that it does not allow the simultaneous use of a pin in a toe in order to stabilize an MTPJ or a DIPJ. Nor does it provide compression across the joint fusion site which would allow for increased stability and thus improve healing. The device affords no rotational stability. Lastly, during clinical application, the device has been known to separate after implantation due to the patient accidently traumatizing the surgical site. Each of these problems is avoided with the use of the shape memory bellows fastener of the present invention.

Another prior art device is a bioabsorbable pin that is placed through the skin through the toe tip across the distal, middle and proximal phalanx of the digit. Like standard pins, they provide no rotational stability to the fusion site and no compression of the fusion site and are thus undesirable.

Other prior art intramedullary osteosynthesis devices are made of a material suitable for deformation by thermal or mechanical action. These devices provide increased stability over the above devices by providing compression at the osteosynthesis sites and may afford some rotational stability although their ability to do so effectively is limited. The dependability of these devices to maintain a strong bite or hold, or maintain alignment on the bones they are implanted into, while at the same time providing compression, has not been satisfactory due to design flaws. These devices also fail to provide the surgeon the option of placing percutaneous wires axially through bones of the phalanx and across the DIPJ and MTPJ when necessary. Furthermore, these devices are difficult to implant into bone due to size and tooling restrictions.

Still other devices are too complex to use or have multiple small parts making them impractical to use in a surgical setting. One such device is made up of two parts that screw into bone first and then screw into each other. However, this is not practicable because the bones of the phalange cannot rotate due to their ligament, tendon, and other soft tissue attachments. Another such device is hinged and allows a rectus or angular placement so the bones of the phalange can be fused straight or at an angle other than 180 degrees. However, multiple small parts make its use impractical and cumbersome.

None of the known prior devices used for the fixation or fusion of interphalangeal joints of the hands or feet are considered sufficient for surgical correction of deformed toes or fingers. The deficiencies include: not providing compression across the fusion site, not anchoring or holding well in bone to provide a firm grasp of the bone such that the device may be easily dislodged after implantation, not cannulated to allow for pinning of the DIPJ or MTPJ when this is necessary, causing nearly complete destruction of the adjacent DIPJ or MTPJ in order to implant the device, requiring very specialized tools for its application such that the implant is not useable without these tools, and/or having very small parts which make the device difficult to use in a clinical setting. These faults result in unwanted sequelae of the intended surgery.

SUMMARY OF THE INVENTION

In accordance with a first embodiment, a fastener comprises an elongated tubular member having a bellows made from a shape memory material and extending along the central aspect of the member for providing compression across two surfaces. The fastener also consists of tubular sleeves made from the same or similar shape memory material extending from both ends of the bellows, each of the two sleeves containing barbs or an anchoring modality to allow the fastener to grab or bite into bone. Shape memory metal alloys have characteristics that allow them to change shape when they go through a temperature change making them particularly useful for this application. The bellows portion of the embodiment as well as the anchoring barbs goes through a shape change allowing the embodiment to perform its function. The barbs change shape to anchor the embodiment in the bone while the bellows changes shape by contracting, in an accordion-like fashion, to pull together and compress opposing faces of the PIPJ.

Many shape memory materials exist. Shape memory metal alloys are probably the most well known and useful. Nitinol is a medical grade biocompatible memory metal alloy made of nickel and titanium currently used in many industrial and medical applications. There are other shape memory metal alloys available. These include but are not limited to alloys composed of iron, nickel, and manganese or iron, manganese, and silicon, some of which are not biocompatible and therefore not for use in human or animal subjects. Many others exist. The shape memory metal alloys have two phases, an austenite phase and a martensite phase. Shape memory metal products are originally manufactured in the austenite phase and annealed to relieve residual manufacturing stresses. The metal may then be cooled sufficiently whereupon it transforms to its highly plastic martensite phase. This phase facilitates manipulation into a new shape by large strain plastic deformation at a low applied stress. The new shape is stable as long as the alloy remains below the phase transition temperature.

The two unique properties described above are made possible through a solid state phase change, that is, a molecular rearrangement, which occurs in the shape memory alloy. Typically when one thinks of a phase change a solid to liquid or liquid to gas change is the first idea that comes to mind. A solid state phase change is similar in that a molecular rearrangement is occurring, but the molecules remain closely packed so that the substance remains a solid.

Raising the temperature of the martensite phase metal to its transition temperature causes the metal to transform back to its austenite phase and thus back to its original shape. In other words, heat acts as a catalyst to cause or induce this shape change. The austenite phase is stable as long as the material is maintained above its transition temperature. Cooling the austenite phase back to its martensite phase after it has been heated, however, does not cause the material to revert back to the previously deformed shape; a deforming force being required.

The preferred embodiments of the shape memory metal bellows fastener are originally manufactured in their austenite phase. The bellows is in a shortened or contracted position (contracted state) and the barbs on the ends of the bellows are displaced radially outward. The fastener is then cooled to its martensite phase and a force is applied to the anchoring barbs forcing them to lie flush or very nearly so, with the tubular sleeves they are attached to. Also a force is applied to the bellows to stretch and elongate the bellows into an extended position (extended state). As long as the fastener remains below its transition temperature, the new shape of the fastener is maintained. The retained memory of the metal fastener allows the deformed device, upon an increase in temperature, to return to its austenite phase. When this happens, the barbs deploy radially outward to embed themselves into the interfacing material and the bellows shortens in an axial fashion, causing the barbs to pull upon the material. The return to the original shortened length of the bellows pulls together any surfaces intended to be compressed together. Thus, the fastener in its martensite phase or extended state may be referred to as a heat responsive fastener that is activated by heat to undergo the transformation from its extended state to its austenite phase or contracted state.

Aside from metal alloys there are other shape changing materials, including plastics. Plastics with these characteristics are often referred to as shape memory polymers, elastic memory composites or shape memory composites, and polymeric smart materials. These polymers have different states similar to the phases of the shape memory metal alloys, and these states are generally referred to as a soft phase or a hard phase. These states are also known as a rubbery state or a glassy state, respectively. The glass transition is the reversible transition from a hard phase (extended state) to a soft phase (contracted state) and is responsible for the shape memory effect of the polymer. These materials also need a catalyst for shape changing which may include heat, electricity, electromagnetic fields, light, or chemical solutions.

The hard or glassy state is the resting state of a shape memory polymer. A product made from shape memory polymer is originally manufactured in the glassy state by conventional methods. The shape memory product is then transformed into its soft or rubbery state by heating or through the use of other catalysts. Once in the rubbery state it is manipulated and deformed into a new shape and held constrained in this new shape. The shape memory polymer product is then cooled wherein it then returns to a glassy state. When the constraining forces are then removed, the polymer maintains this newly shaped glassy state. The product is then ready for use based on a utility for which it has been designed or created. For instance, the shape memory polymer product may be implanted into a body wherein body heat or some other catalyst has an effect on the newly shaped glassy product causing it to return back to its rubbery state. This last transition from the glassy state to the rubbery state also causes the product to change back to its original shape. These changes in shapes can be used to do work or cause an effect on the tissues surrounding it.

Some of the shape memory polymers have the ability to take on two, three, and maybe even four shapes and they can have a wide range of properties, from stable to biodegradable or elastic to rigid. Polymers that show shape memory effects include polyurethane, polyethylene oxide, and polyethylene terephthalate, among others. For example, poly(ε-caprolactone) dimethacrylate and n-butyl acrylate are biodegradable and can be made to change shape through the use of heat from a laser. Fasteners according to the invention made with these shape memory polymers could be used in some applications.

Some embodiments of the fastener provide angularity between the tubular members, and still other embodiments demonstrate that the tubular members do not need to be made of shape memory material entirely but may instead be of standard surgical materials and joined by bellows of shape memory material. The invention also includes fastening methods and medical procedures using the bellows fasteners described herein.

One or more aspects of the invention are as follows: to allow compression across an object's surfaces, to prevent slipping or accidental displacement of the implant, to intrinsically afford rotational and torsional stability, and to prevent destruction of adjacent joints. Several embodiments provide a cannulation for accurate placement, rapid placement, and the option of maintaining a pin across adjacent surgical sites if needed. Other aspects will be apparent from review and consideration of the drawings and description. Also, most of the tools required for the placement of the fastener are readily available in most operating rooms, negating the need for large amounts of specialized tooling.

The problems these embodiments resolve as pertains to osteosynthesis include: providing reliable compression across a fusion or osteosynthesis site, preventing unwanted distraction of an osteosynthesis site, provide rotational stability, preventing the destruction of adjacent joints, and allowing the option for a wire to remain in the surgical site and adjacent surgical sites at the same time as the invention if the surgeon so desires.

BRIEF DESCRIPTION OF THE DRAWINGS

The invention may be further understood with reference to the accompanying drawings, which are briefly described as follows:

FIG. 4A is a perspective view of the first embodiment of the fastener in its martensitic phase showing a guide wire being introduced into one end of the embodiment.

FIG. 4B is a perspective view of the fastener of FIG. 4A in its austenitic phase with a guide wire passing centrally all the way through the hollow core of the fastener's long axis. The guide wire can be passed through the embodiment in either its martensitic or austenitic phases.

FIG. 4C is an enlarged perspective view of one end of the embodiment as shown in FIG. 4B detailing the guide wire passing into the end of the fastener and the barbs of the fastener deployed outward in their austenitic phase.

DETAILED DESCRIPTION OF THE INVENTION

The invention is a fastener that provides axial compression of two opposing surfaces. The fastener is generally a linear, cylindrical tube made in whole or in part of shape memory metal, super elastic metal, or other material having similar shape changing characteristics. The central portion of this tube takes the shape of a bellows and preferably is made of a shape memory metal. The shape memory metal may be an alloy produced or made in its austenite phase and annealed to relieve residual manufacturing stresses. Subsequently, a change to a martensitic phase can be induced in the shape memory alloy by sufficiently cooling the metal. In the martensite phase, the bellows is plastically deformed into an elongated shape, which is its extended state. Additionally, anchoring barbs are plastically deformed to lie flush, or approximately so, with the tubular sleeves. The low temperature is maintained and functions to maintain the deformed shape until implantation. The shape memory of the metal allows the deformed device, upon an increase in temperature, to deploy the barbs radially outward to embed themselves into the interfacing material and the bellows to shorten in an axial fashion, causing the barbs to pull upon the material and compressing together any surfaces intended to be compressed together.

As an example of its use, the fastener may be implanted into opposing bone surfaces of a resected joint of a finger or a toe and a change in shape of the memory metal after implantation causes the two bone surfaces to be drawn and compressed together. The compression imparts a resistance to be being pulled apart as well as resistance to axial rotation, shearing and side to side bending. The forces from the shape change in the bellows are transmitted through the barbs into the bone they are embedded into, pulling the bone together as the bellows contracts. These barbs also add to the rotational stability of the fastener and offer resistance to distractive forces across the fusion surfaces which would delay bone healing. As described in the following embodiments, the fastener may be used for joining together the ends of bones, repair of bone fractures, or stabilizing surgically-induced bone cuts. The embodiments may also be used for joining or coupling other objects as well, such as a piece of plywood to a cement wall or a piece of plastic to a piece of metal, two wood surfaces, or a tooth to a bone.

First Embodiment

Figure 2A:
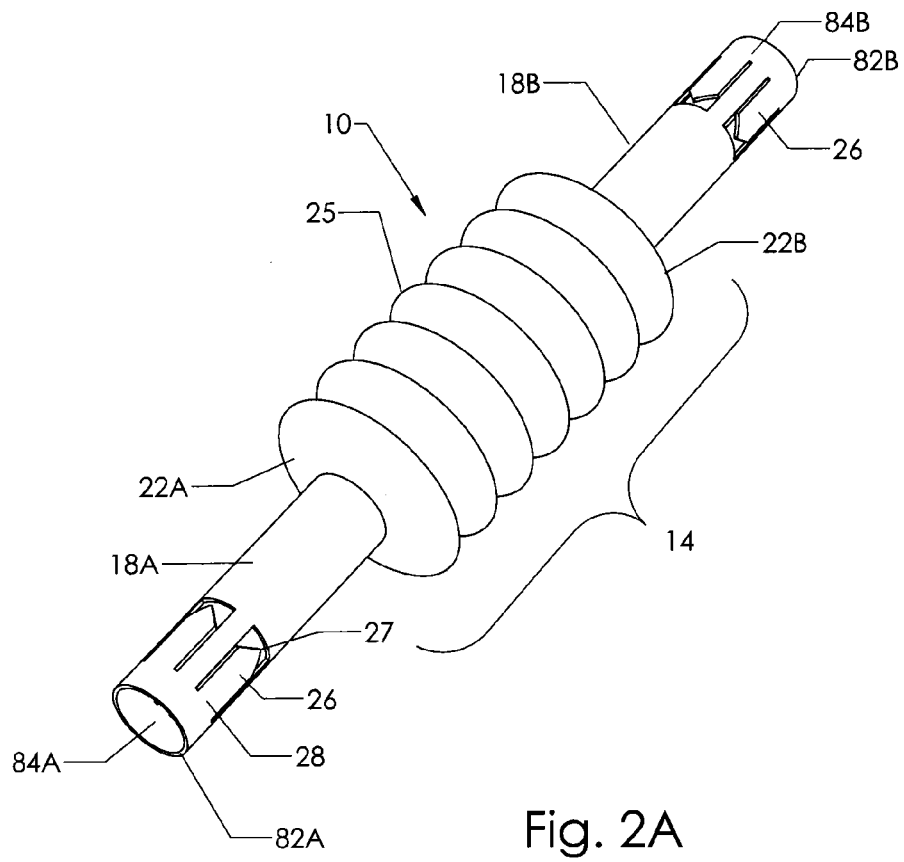
FIG. 2A is a profile perspective view of a first embodiment of a fastener according to the invention as shown in its martensitic phase. The fastener is in its elongated stressed phase where the central bellows is stretched and barbs at the ends of the fastener lie flush with the walls of sleeves integral with and extending outward from the bellows.
Figure 2B:
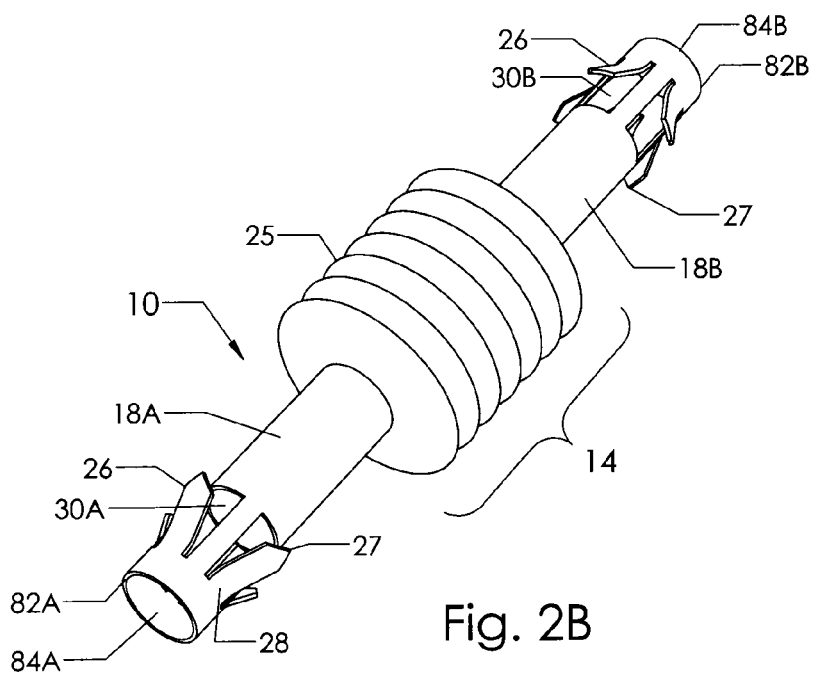
FIG. 2B is a profile perspective view of a first embodiment of the fastener which has gone through a shape change from the martensitic phase of FIG. 2A to its axially shortened austenitic phase. This is the resting shape of the fastener and also the shape of the fastener after implantation into a toe or bone or other substrate. Here the central bellows has shortened axially and the barbs have deployed outwardly from the long axis of the fastener.

A first embodiment of a fastener 10 according to the invention is shown best in FIGS. 2A and 2B, and FIGS. 4A and 4B. FIGS. 5A-5H are side elevation views of the stepwise operation of the first embodiment. Fastener 10 is made of a shape memory metal alloy such as Nitinol, commonly used in medical applications, but other shape memory alloys and shape memory polymers could be used for non-medical applications. Shape memory alloys have two phases, an austenite phase and a martensite phase. Fastener 10 is originally manufactured in its austenite phase which is shown in FIG. 2B. After fastener 10 is manufactured, it is cooled to its martensite phase to allow it to be changed by deformation from its original shape to the new shape shown in FIG. 2A. As long as fastener 10 is kept cooled, it will remain in the deformed martensitic phase of FIG. 2A.

Figure 3:
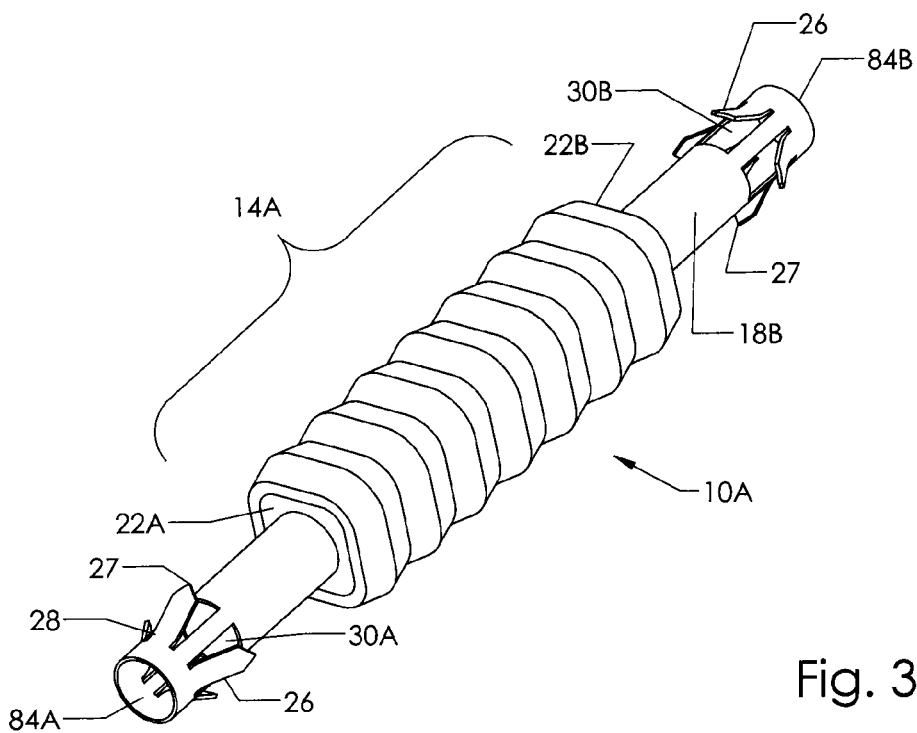
FIG. 3 is a perspective view of an alternative embodiment of the fastener in its martensitic phase. It shows the bellows portion of the fastener as an elongated square bellows instead of an elongated cylindrical or tubular bellows.

In a first embodiment, the fastener 10 is generally tubular or cylindrical in design and is symmetrical around its longitudinal axis. In the central aspect of fastener 10, the tubular shape is expanded into a folded, pleated or corrugated shape, hereinafter referred to as pleated, taking the form of a bellows 14. FIG. 3 shows an alternative to this embodiment wherein the expanded shape is generally square, but other cross-sectional shapes may be used as well, such as oval, rectangular or triangular, but all of these shapes are still pleated along the longitudinal axis of the bellows. The cross-sectional shape selected preferably has a continuous periphery, although the periphery could be segmented where all or a portion of the bellows is formed by strips of shape changing material.

As shown in FIG. 2A, bellows 14 has a first end face 22A and a second end face 22B that serve as the ends of the bellows. Bellows 14 consists of a plurality of pleats 25, the number of such pleats controlling the development of the compressive force and the length change of the embodiment after the bellows undergo a shape change. Extending axially outward from end faces 22A and 22B of bellows 14 are further elongated tubular structures 18A and 18B respectively, hereinafter called sleeves 18A and 18B. Sleeves 18A and 18B have distal ends 82A and 82B, respectively, as shown best in FIGS. 2A, 2B and 4C, which are opposite the sleeve end attached to the bellows and serve as the terminal ends of the fastener (hereinafter termed the terminal ends 82A and 82B). Terminal ends 82A and 82B are preferably circular and the axis through the centroid of each circular area is parallel and coincident with the long axis of the fastener. As seen best in FIGS. 2A-2C, terminal ends 82A and 82B each have a centrally placed portal 84A and 84B. Portals 84A and 84B are the beginnings of central longitudinal and cylindrical lumens or passages 30A and 30B. As seen best in FIGS. 2B and 2C, these lumens pass from the terminal ends 82A and 82B axially through the center of sleeves 18A and 18B, respectively. Hereinafter, lumens 30A and 30B will be termed cannulations 30A and 30B.

Figure 2C:
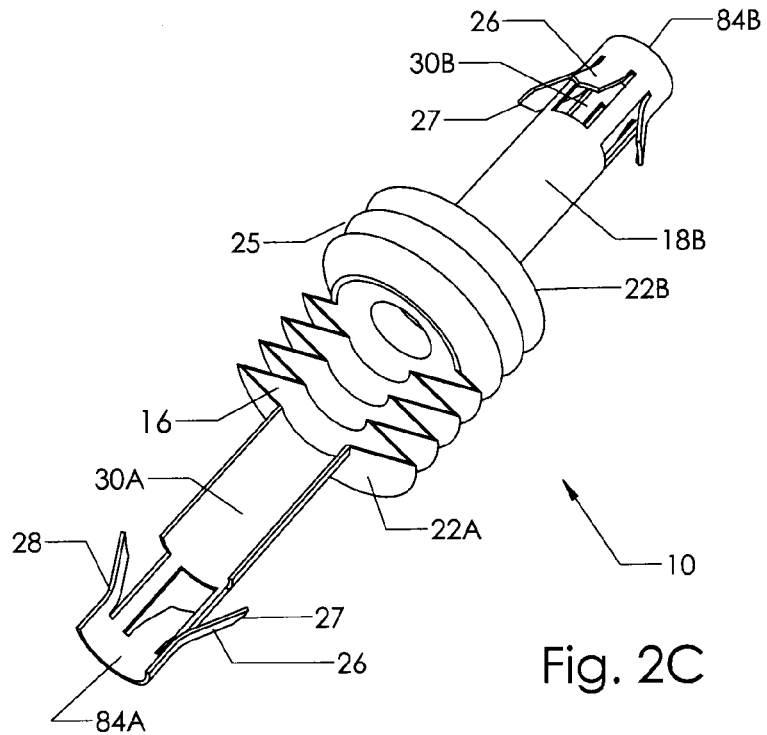
FIG. 2C is a profile perspective view with partial cut away of the fastener in FIG. 2B in its austenitic phase showing the internal aspect of a main embodiment.

Sleeves 18A and 18B and cannulations 30A and 30B are all axially aligned with each other. FIG. 2C shows the internal makeup of the main embodiment. The hollow internal diameter of bellows 14 is termed chamber 16. Cannulations 30A and 30B become contiguous with chamber 16 where sleeves 18A and 18B meet the end faces 22A and 22B of bellows 14. These are axially aligned such that a straight wire can be passed through portal 84A and cannulation 30A of sleeve 18A, continue through chamber 16, and further through cannulation 30B of sleeve 18B, and finally passed out of portal 84B. As shown best in FIGS. 4A, 4B, and 4C, portals 84A and 84B and cannulations 30A and 30B have a diameter sufficient to accommodate a guide wire 34, which can be used during a surgical procedure. The cannulation diameter is preferable only slightly larger than the wire diameter to precisely guide axial transport of the sleeves 18A and 18B and thereby insure accurate placement of the fastener 10 within the bones to be joined. Chamber 16 has an equal or greater diameter to accommodate guide wire 34.

As seen best in FIG. 2A, set inward from distal ends 82A and 82B along the length of each sleeve 18A and 18B are a plurality of tabs 26 cut into each sleeve and shown in their cold state with their surfaces aligned with the surfaces of the sleeves. These tabs will hereinafter be called barbs 26, because of the purpose they serve in their heated state of anchoring fastener 10 into a bone substrate and thereby preventing the fastener from being pulled out when axial stress is applied to the fastener. In other words, the barbs 26 transform the terminal ends 82A and 82B into anchoring members. FIGS. 2B and 2C show four barbs 26 evenly spaced from each other around the periphery of each sleeve, and in their heated and expanded state wherein they are slanted substantially outward from the fastener axis in the direction of end faces 22A and 22B of bellows 14. At least one and preferably two or more barbs would be acceptable for this embodiment and the other embodiments described herein. Multiple barbs could also be offset from each other length-wise along the sleeves or circumferentially around the outer periphery of the sleeves such that one could conceivably have six, eight or more of these barbs per sleeve.

In forming barbs 26, each sleeve 18A and 18B is cut through its full wall thickness from the external side of its outer diameter to the internal cannulation 30A and 30B, as most notably seen in FIG. 2C. Each barb 26 thus has the same thickness as the wall of sleeves 18A and 18B and, being cut from the metal of the sleeves, the outer and inner surfaces of the barb in its retracted position are substantially flush with the outer surface of the sleeve and the inner sleeve surface defining the cannulation, respectively, when the sleeve is in its cold or martensitic phase.

Thus, each barb 26, being made from shape memory metal and in its cooled martensitic phase, lies parallel to the long axis of fastener 10. As best shown in FIGS. 2C and 4C, barb 26 has a proximate end set outward from bellows 14 closest to terminal ends 82A and 82B of sleeves 18A and 18B, which will be called base 28. Base 28 functions as the hinge point of barb 26 when the barb goes through its shape change. Set opposite base 28 and substantially towards bellows 14 along the length of barb 26 is a distal end portion in the form of an apex 27, which is generally pointed or arrowhead shaped.

Like the bellows, barbs 26 will undergo a shape change when transforming from a cooled martensite phase to an austenite phase as they are warmed to body temperature. This process is best seen in FIG. 2A, wherein fastener 10 is in its martensite phase, and FIG. 2B, wherein fastener 10 has changed back to its austenite phase. In so doing, each barb 26 will curl or bend outward away from the central longitudinal axis of fastener 10. Base 28 serves as the pivot or bending point for each barb. Apex 27 is designed to help the barb cut into or push its way into the surrounding substrate that fastener 10 is being implanted into in order to anchor fastener 10 and prevent its rotation or pull-out. During this warming process, bellows 14 axially shortens during the change from its martensite phase to the austenite phase as shown best in the shape change from FIG. 2A to FIG. 2B. Alternatively, barbs 26 may be partially deployed in their cold state by being partially bent outwardly at time of insertion into bone in order to mitigate slipping of the fastener and prevent accidental pullout before being fully deployed.

Operation of First Embodiment

Fastener 10, as well as the other embodiments described herein, may be made from a shape memory alloy, such as Nitinol, though there are other shape changing materials available that also may be used. When any of these embodiments are used, say for a surgical procedure like a hammertoe correction, the properties of the metal or other material allow it to exist in different shapes at different temperatures. For example, when the Nitinol embodiment is moved from a cool or cold state, at which time it is in its martensite phase, and then implanted in the body and warmed to body temperature, it will undergo a change in its shape as it transforms to its austenite phase.

As shown again in FIGS. 2A and 2B, bellows 10 will shorten along its axial length, like an accordion, during its phase change from a martensitic phase to an austenitic phase. At the same time, barbs 26 on sleeves 18A and 18B will go through a phase change as well, expanding radially outward from their base 28 such that they will anchor the embodiment into a substrate, for example, the bones of a proximal and middle phalanx of a toe or finger. This axial shortening of bellows 10 provides the necessary compressive force to draw together two bone ends that have been surgically prepared or fractured.

Figure 1A:
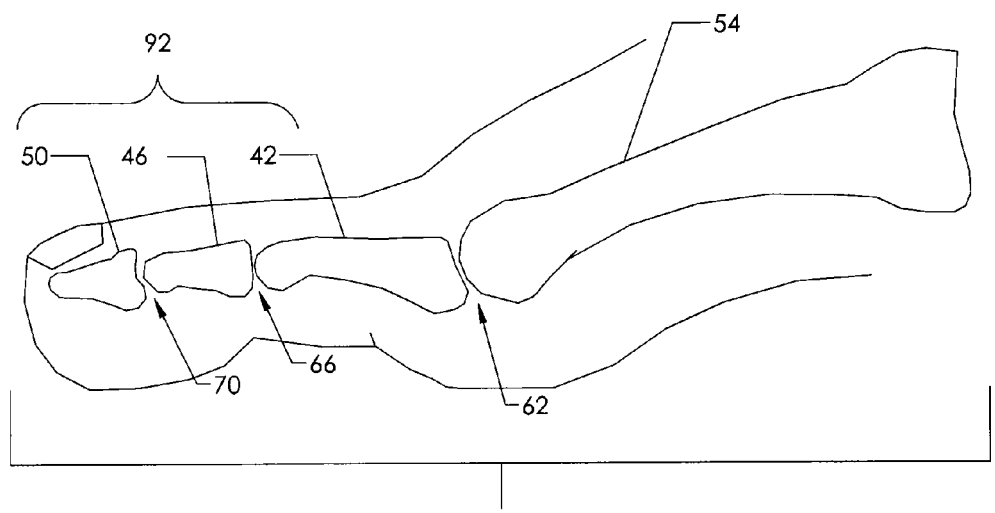
FIG. 1A is a side elevation view of what a normal toe should look like, demonstrating three phalangeal bones that make up the toe and a metatarsal bone of the foot that articulates with the toe, the toe being linear across the joints with no flexion or extension contractures.

FIG. 1A demonstrates a normal toe which is made up of multiple bones. The parts of a normal toe include a metatarsal bone 54 and a proximal phalanx 42. Together the articulation of metatarsal bone 54 and proximal phalanx 42 make up a metatarsal phalangeal joint 62 or MTPJ 62. More distally along the toe, a second articulation is made between proximal phalanx 42 and a middle phalanx 46. This articulation constitutes a proximal interphalangeal joint 66 or PIPJ 66. Even more distally along the length of the toe, a third articulation occurs between middle phalanx 46 and a distal phalanx 50. This articulation constitutes a distal interphalangeal joint 70, or DIPJ 70. Anatomically, a normal toe lies in a straight or linear fashion along its length from metatarsal bone 54 to the distal end of distal phalanx 50, as shown best in FIG. 1A. PIPJ 66 and DIPJ 70 generally have no substantial angular deformity while MTPJ 62 normally rests at about a 15 degree angle.

Figure 1B:
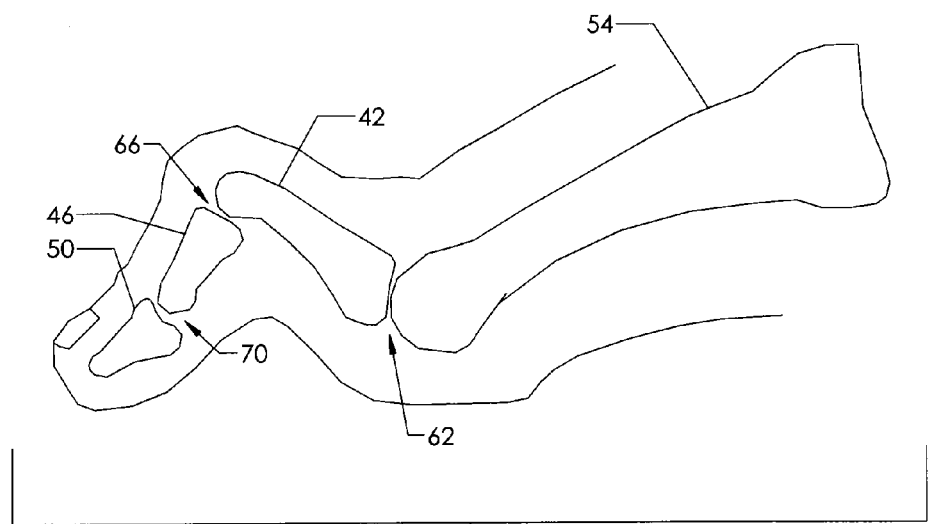
FIG. 1B shows a side elevation view of a hammertoe where the toe is non-linear. There are extension and flexion contractures of the joints of the toe effectively causing the toe to be crooked.

Looking at FIG. 1B, one can see a hammertoe, a toe that is deformed or not straight. Here the toe has angular contraction deformities at the joints along the length of the toe. In a classic hammertoe deformity, as demonstrated in FIG. 1B, there is a contracture of MTPJ 62 well beyond a normal 15 degrees whereby proximal phalanx 42 is upwardly displaced on metatarsal bone 54. Tight ligaments and tendons, not shown, facilitate holding the deformed MTPJ 62 in this position, contributing to the toe's pathology. Then, looking at PIPJ 66, middle phalanx 46 is contracted downward. Again, tight ligaments and tendons facilitate holding deformed PIPJ 66 in this position. Lastly, at DIPJ 70, distal phalanx 50 is contracted upward in relation to the downward positioned middle phalanx 46. Yet again, tight ligaments and tendons facilitate holding the deformed PIPJ in this position.

Figure 5A:
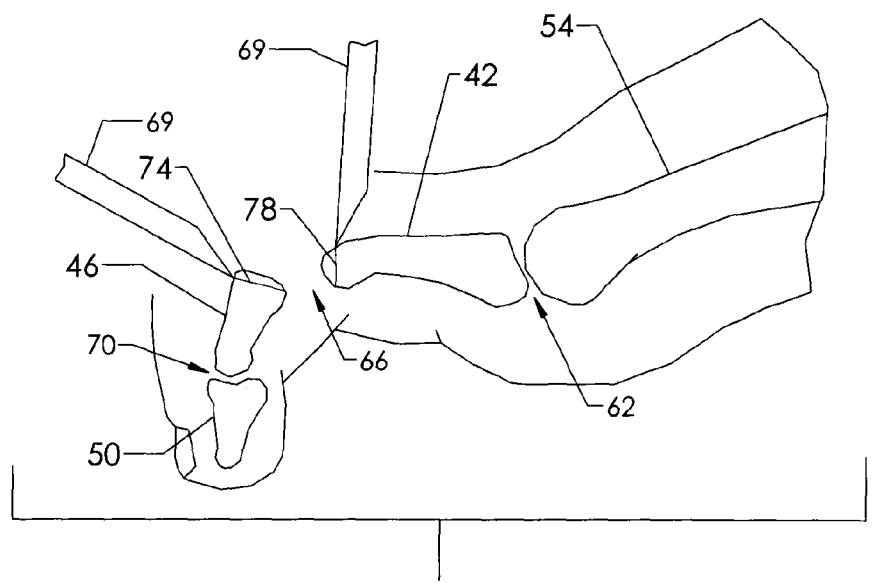
FIG. 5A is a side elevation view of a toe wherein the proximal interphalangeal joint has been surgically opened and a cutting blade demonstrates the resection area of bone from the proximal phalanx and middle phalanx that comprise the joint.

In the surgical correction of a hammertoe, the general principle is to address the primary deformity at the level of PIPJ 66. To do so requires making a surgical incision over PIPJ 66, dissecting the soft tissues down to the ligaments and tendons of the joint, and cutting these to reflect them out of the way such that the surgeon can access the bones of PIPJ 66, namely proximal phalanx 42 and middle phalanx 46. Herein below is the application of the first embodiment. The application and operation can best be seen in FIGS. 5A through 5H. FIG. 5A shows a hammertoe where surgical exposure of the bones of PIPJ 66 has been performed. A surgical saw 69 is used to cut the articulating portion of bone from proximal phalanx 42, perpendicular to its long axis, effectively producing a flat cut surface 78 of proximal phalanx 42. Subsequently a surgical saw is again used and the articulating portion of bone from the middle phalanx 46 is cut away, producing a flat cut surface 74 of middle phalanx 46. The flat cut surfaces 74 and 78 are sometimes referred to hereinafter as abutment surfaces.

Figure 5B:
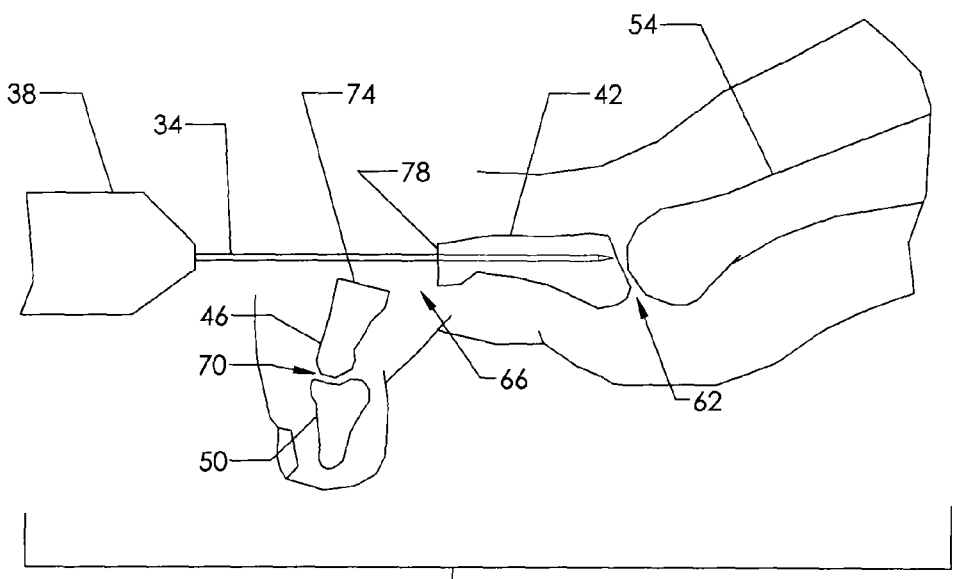
FIG. 5B is a side elevation view showing the joint surfaces resected and creating a flat surface for the two bones to abut against each other. A guide wire has been introduced through the flat resected bone surface of the proximal phalanx and passed or driven down the central axis of the phalanx.
Figure 5C:
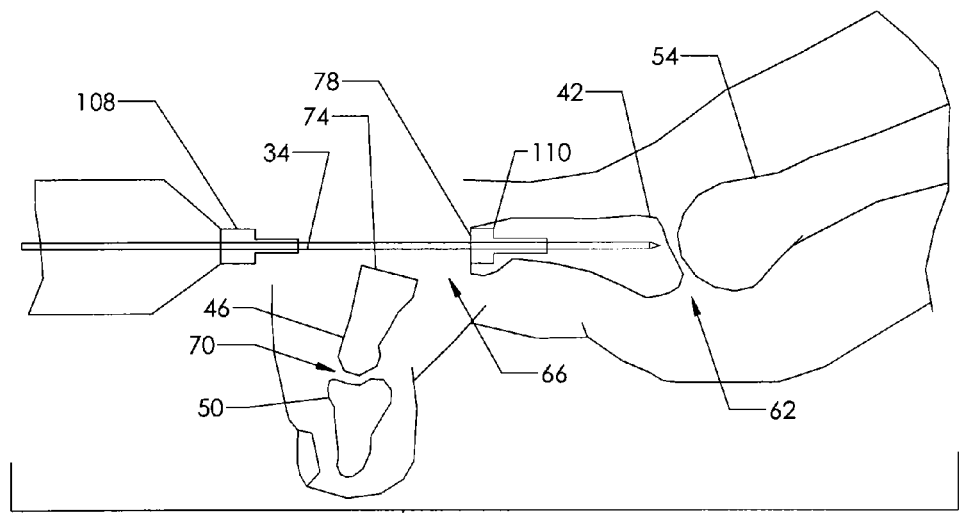
FIG. 5C is a side elevation view showing the guide wire still in place in the proximal phalanx. A counter-borer has been placed over the guide wire and driven into the proximal phalanx, reaming the bone to create a void for placement of the fastener.

In FIG. 5B, a guide wire 34 attached to a wire driver 38 is then inserted into the abutment surface 78 of proximal phalanx 42 and advanced down the center of proximal phalanx 42 to the area of MTPJ 62 but not into it. Wire driver 38 is then removed from over guide wire 34. As shown in FIG. 5C, a counter-borer 108, cannulated like fastener 10, is then slid over guide wire 34 and used to ream out some of the bone from proximal phalanx 42, leaving a hollow tubular shape or bore in the bone matching the shape of approximately one-half the length of fastener 10. Hereinafter, this matching hollow tubular bore will be termed bore hole 110. If one of the non-round embodiments is used, say a square or triangular embodiment, a similarly shaped broach may be used instead of a counter-borer. Counter-borer 108 is then removed from proximal phalanx 42 and guide wire 34 is subsequently removed with wire driver 38.

Figure 5D:
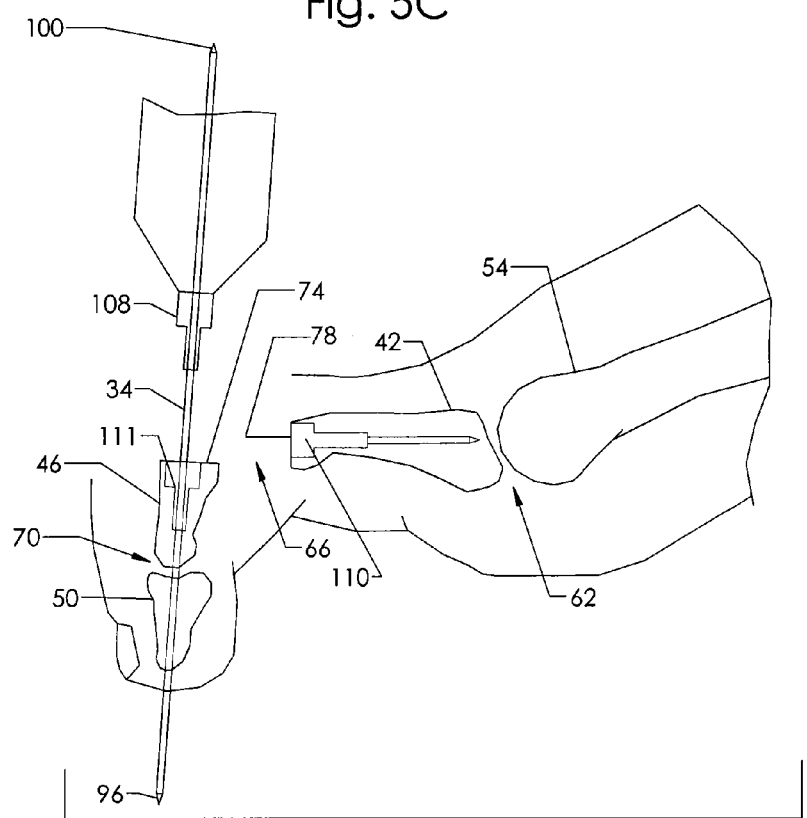
FIG. 5D is a side elevation view showing the guide wire removed from the proximal phalanx and inserted into the middle and distal phalanx and sticking out passed the end of the toe. The counter-borer has been placed over the guide wire and the middle phalanx reamed with the counter-borer, creating a void for placement of the fastener in the middle phalanx.
Figure 5E:
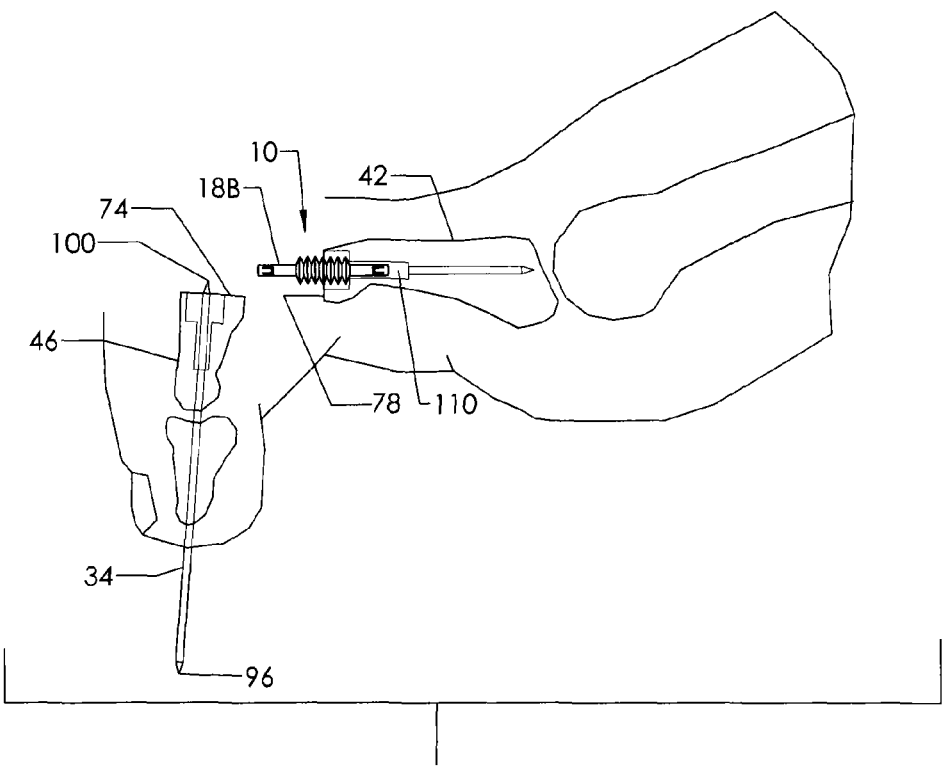
FIG. 5E is a side elevation view showing the guide wire repositioned in the toe so that its tip sits just proud of the resected bone surface of the middle phalanx. The view also shows a first embodiment of the fastener in its martensitic phase inserted into the bore hole created in the proximal phalanx.

In FIG. 5D, guide wire 34 is placed into the center of abutment surface 74 of middle phalanx 46. Guide wire 34 is then driven axially down the central long axis of middle phalanx 46, driven across DIPJ 70 into distal phalanx 50, and then out through the skin on the end of the toe. The wire driver 38 is then removed from a proximal end 100 of guide wire 34. Counter-borer 108, shown in FIG. 5D, is then slid over proximal end 100 of guide wire 34 and used to bore into middle phalanx 46, producing a hollow tubular shape that matches the other one-half of fastener 10, hereinafter termed bore hole 111. It is also contemplated for this embodiment and those described herein below that the respective sleeves and corresponding portions of the bellows of the fastener may differ from each other in size, length and/or shape with corresponding differences in their bore holes. Counter-borer 108 is removed from guide wire 34 and, as shown in FIG. 5E, using wire driver 38, guide wire 34 is then advanced further out the end of the toe so that proximal end 100 of the guide wire is sitting just proud of abutment surface 74 of middle phalanx 46. Up until this point, the fastener has been previously sterilized and has been kept refrigerated so as to maintain the fastener at its martensite phase, elongated and the barbs lying flush with the sleeves of the fastener.

Figure 5F:
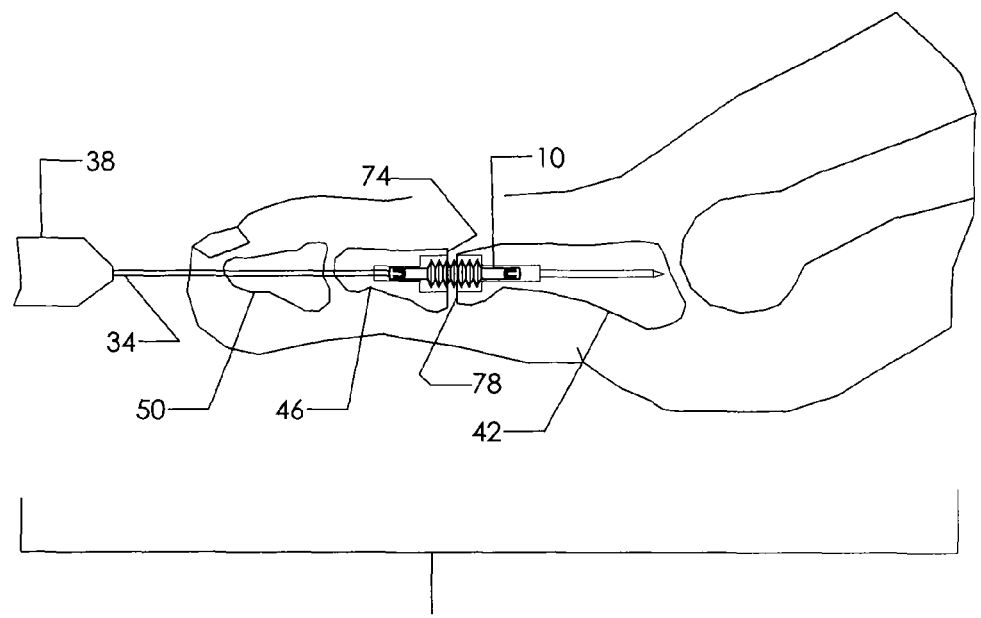
FIG. 5F is a side elevation view showing that the toe has been manipulated and reduced into position wherein the tip of the guide pin just proud of the middle phalanx has been inserted into the end of the first embodiment of the fastener and the fastener inserted into the void of the middle phalanx. The fastener is still in its martensitic phase. The adjoining surfaces of the proximal and middle phalanx have not yet been compressed together.

FIG. 5E shows fastener 10 imparted into matching bore hole 110 of proximal phalanx 42. The surgeon then manipulates the bones by grabbing proximal phalanx 42 and middle phalanx 46 and raising middle phalanx 46 upward and placing proximal end 100 of guide wire 34 into sleeve 18B of the fastener. Middle phalanx 46 is then press fitted onto sleeve 18B and the portion of fastener 10 that remains protruding from proximal phalanx 42. As middle phalanx 46 is imparted onto fastener 10, guide wire 34 passes along cannulation 30B of the fastener. As shown in FIG. 5F, abutment surface 78 of proximal phalanx 42 and abutment surface 74 of middle phalanx 46 are then manually approximated together such that they are contacting each other. At this point, the proximal phalanx 42, middle phalanx 46, and distal phalanx 50 are all now aligned straight and the fastener 10 warms to body temperature.

Figure 5G:
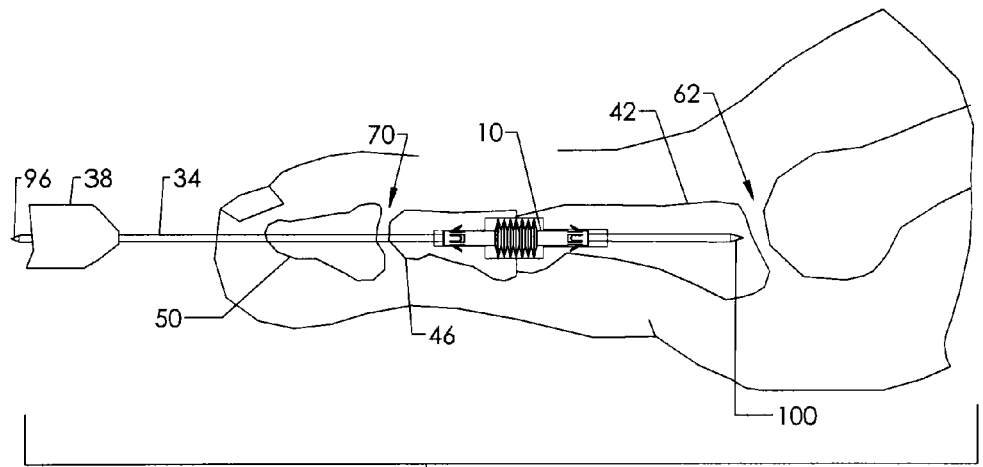
FIG. 5G is a side elevation view of the fastener having undergone its phase change and is now in its austenitic phase. The barbs on the fastener have deployed into the bone and the bellows has compressed the bone surfaces together via its shape change. The guide wire has also been driven all the way into the proximal phalanx.

As the fastener 10 warms to body temperature, it changes from its cooled martensite phase to its warmed austenite phase, undergoing a shape change. In so doing, barbs 26 deploy by expanding radially outward from the central axis of the cannulation 30 and embed themselves into the bone of the surrounding proximal phalanx 42 and middle phalanx 46. Transitioning from FIG. 5F, FIG. 5G shows that as this process occurs, the bellows, in accordion fashion, shortens along its axial length, drawing together into abutment and compressing together the cut surface 74 of middle phalanx 46 and the cut surface 78 of proximal phalanx 42. This compressive force across the middle and proximal phalanx provides necessary stability to allow the two bones to heal together. It is at this point that the surgeon will decide if the procedure is complete. If he or she feels the procedure is complete, the guide wire 34 is removed from the toe as facilitated by use of wire driver 38 on distal end 96 of guide wire 34. Then layered closure of the tendon, ligaments, and skin is performed. Fastener 10 remains in place to provide stability during healing.

Figure 5H:
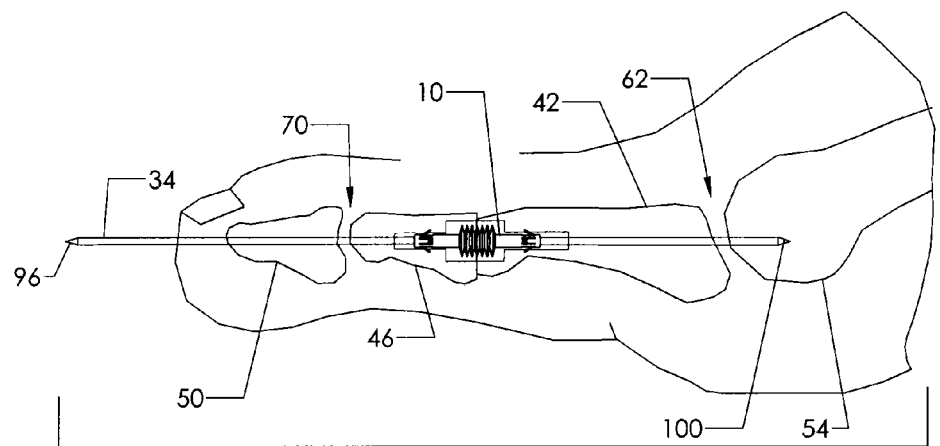
FIG. 5H is a side elevation view showing the fastener again in position across the proximal interphalangeal joint and having compressed together the bone surfaces. The guide wire has been driven across the metatarsal-phalangeal joint into the metatarsal, stabilizing the joint.

There are times however when the surgery is not complete at this point. Oftentimes adjunctive procedures are performed on DIPJ 70 and MTPJ 62 at the same time as the osteosynthesis procedure on PIPJ 66. Typically these procedures involve tendon or ligament surgery, or sometimes cutting of bone. Osteosynthesis is rarely performed on DIPJ 70 or MTPJ 62 but the tendon and ligament procedures that might be performed can leave the joints unstable due to soft tissue imbalances. If the surgeon decides that she or he needs to afford stability to these joints as well, then she or he may decide to utilize another important function of fastener 10, that being cannulation 30, which will allow guide wire 34 to be left within the toe during healing along with fastener 10. As shown in FIG. 5H, instead of removing guide wire 34 after the fastener has gone through its shape change, a surgeon may advance guide wire 34 through cannulation 30 and across MTPJ 62 into metatarsal 54, providing stability to MTPJ 62 so that it cannot be moved during the healing process. Instead, the surgeon may leave the guide wire 34 in place across DIPJ 70 without crossing MTPJ 62, as best shown in FIG. 5G. This then affords stability only to DIPJ 70, if necessary. The distal end 96 of guide wire 34 is then left sticking out the end of phalanx 50. The wire is left in this position for approximately 4-6 weeks after the surgery while osteosynthesis or fusion occurs across proximal phalanx 42 and middle phalanx 46. After healing has occurred, the surgeon may remove guide wire 34 in their office by grasping the exposed distal end 96 with a pliers and pulling it out, thus negating a return to the operating room.

Second Embodiment

Figure 6A:
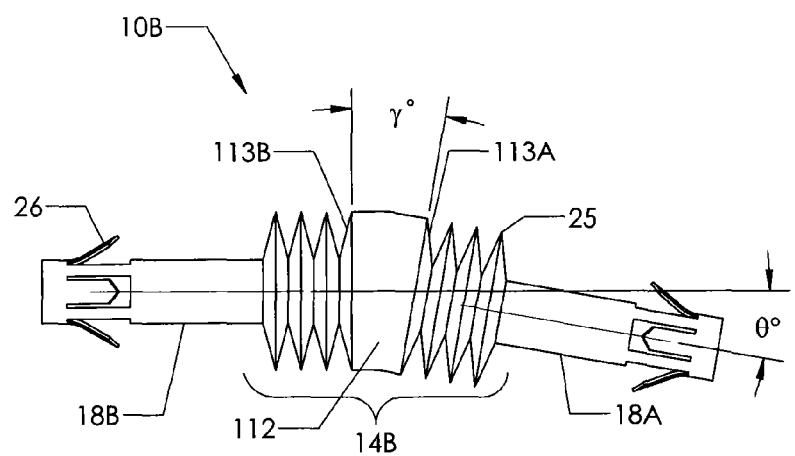
FIG. 6A is a side elevation view showing an alternative embodiment of the fastener wherein the fastener is angled to allow fusion of the proximal interphalangeal joint at an angle.

Hereinabove has been set out a first embodiment for a shape memory metal bellows fastener. A second embodiment allows for angular positioning of the middle and proximal phalanx of the toe. As shown in FIG. 6A, a fastener 10B is not linear but rather angled and is seen here in its austenite phase, having shortened from an elongated position and barbs 26 having expanded outward as already described hereinabove. In this figure, the angularity of the fastener occurs in the mid-portion of bellows 14B. Situated substantially towards the middle of bellows 14B, one of pleats 25 of bellows 14B is replaced by a boss 112, wherein the ends of the boss are angled relative to each other instead of being parallel. Boss 112 has an end face 113A that is positioned closest to sleeve 18A and an end face 113B positioned closest to sleeve 18B. Boss 112 may divide the bellows approximately into two equal halves. However, boss 112 may instead replace the first pleat or be situated anywhere between the first pleat and the last pleat.

Boss 112 is symmetric about a plane whose normal direction is inclined at an angle to the axis of sleeve 18A and inclined at an equal angle to the axis of sleeve 18B, causing end faces 113A and 113B to slope towards each other, creating an angularity $\gamma$ to the embodiment. Sleeves 18A and 18B are thus no longer coaxial in this embodiment and the angularity of boss 112 is translated to an angular relationship $\theta$ between the sleeves. Angle $\gamma$ equals angle $\theta$. Most surgeons prefer to fuse a toe straight or at zero degrees while some may prefer a ten to fifteen degree angle. When it comes to fingers, the joints are often fused at greater angles and so the embodiment may need an angularity of greater than fifteen degrees, such as twenty degrees to fifty degrees for a functional result. It is further contemplated that sets of fasteners may be provided to give boss angularities preferably at least between 1° to 15°, more preferably 1° to 45°, most preferably 1° to 60°, and preferably in increments of 5°.

Operation of Second Embodiment

The application of the second embodiment requires the proximal phalanx and the middle phalanx to be prepared with angular cuts. The cut surface of the proximal or middle phalanx, instead of being cut perpendicular to the long axis of the bone, is cut at an angle to the long axis. The sum of the angles cut into both phalanxes is such that it matches the built-in angle of the embodiment; say ten to fifteen degrees for a toe or whatever the angle of the embodiment.

Figure 6B:
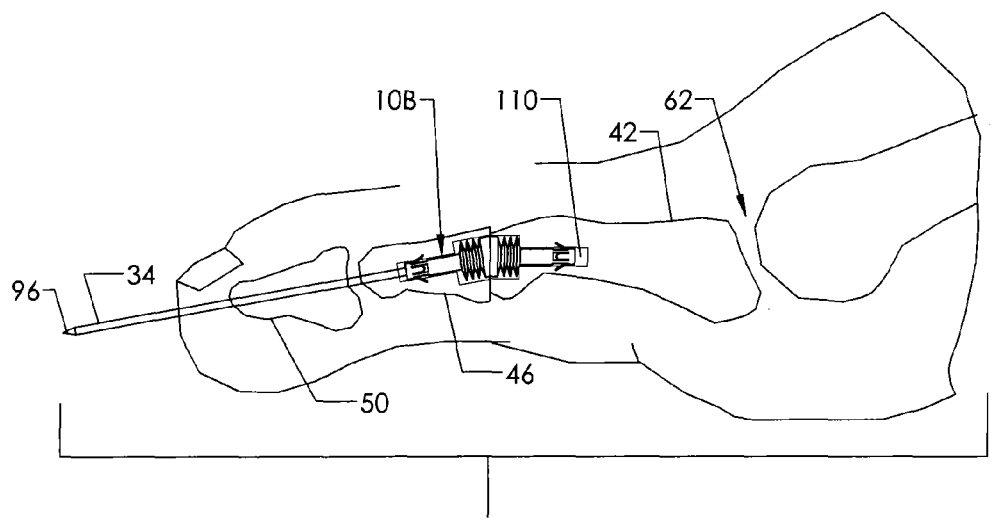
FIG. 6B is a side elevation view showing the alternative embodiment of FIG. 6A placed in the proximal interphalangeal joint, fusing the bones together at an angle.

The step wise application of the embodiment is otherwise the same as FIGS. 5A through 5F. The proximal phalanx is cut and the middle phalanx is cut, each at one-half of the desired full angle. A guide wire is placed axially into the proximal phalanx and the phalanx is then counterbored to create a hole for the implant. The guide wire is then removed and driven axially into the middle phalanx and out the end of the toe. Again the guide wire is positioned so that it is nearly flush with the cut surface of middle phalanx or slightly protruding. A counter-borer is then placed over the guide wire and a hole created to appropriate depth to match one-half the shape of the second embodiment. FIG. 6B shows the angled fastener in place in a toe with a slight angularity to the fusion site. The guide wire is then left in place or it can be removed at this point. Fastener 10B is inserted into matching bore hole 110 of proximal phalanx 42. Middle phalanx 46 is positioned onto the portion of fastener 10B that remains protruding from the proximal phalanx 42, all in similar fashion as described for the first embodiment.

As the middle phalanx 46 is installed onto fastener 10B, guide wire 34 is free to pass along cannulation 30 of the fastener up to the point where the angularity prevents it from passing any further and so this embodiment is more desirable when pinning of the MTPJ 62 is not necessary. Cut surface 78 of proximal phalanx 42 and cut surface 74 of middle phalanx 46 are manually held together such that they are in intimate contact with each other until fastener 10B goes through its shape change. Thus, other than the bone cuts and angular shape of fastener 10B, the function of the embodiment is the same as the first embodiment.

Third Embodiment

Figure 7A:
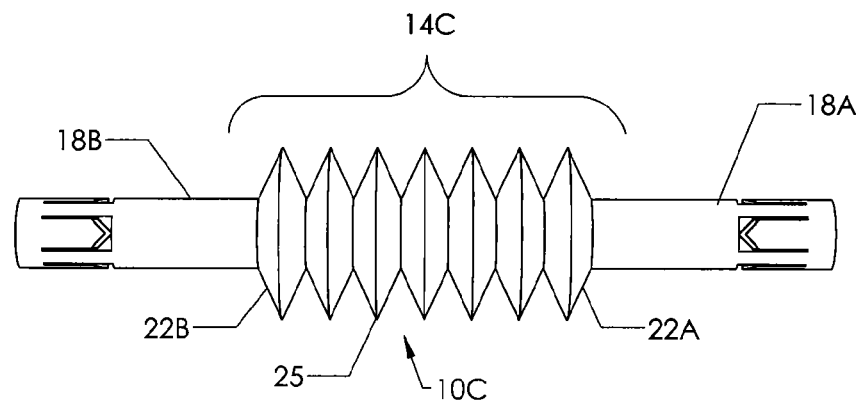
FIG. 7A is a side elevation view of an alternative embodiment of the fastener wherein it seemingly is identical to the main embodiment and is shown in its martensitic phase. However, this second alternative embodiment goes through an angular shape change built into the bellows as will be seen in FIG. 7B.
Figure 7B:
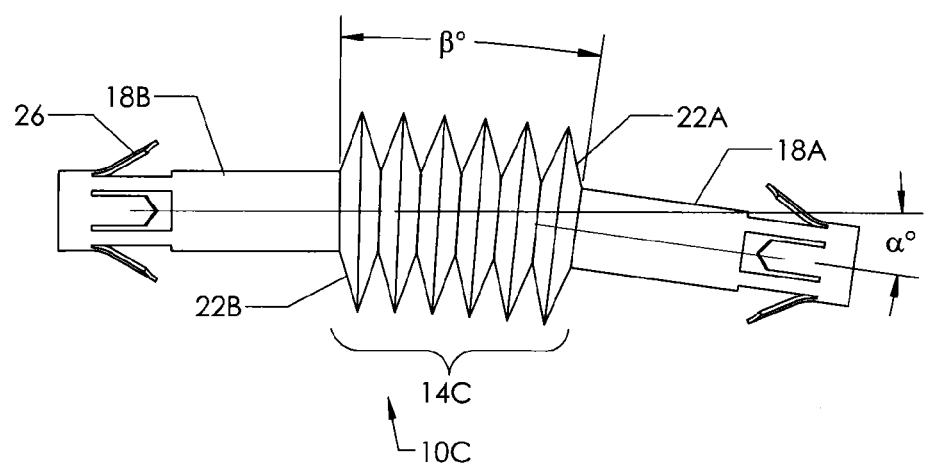
FIG. 7B is a side elevation view of the embodiment of FIG. 7A wherein the fastener is shown in its austenitic shortened phase and has also undergone an angular change for the purpose of fusing a toe in an angular position.

FIGS. 7A and 7B show another alternative embodiment wherein a fastener 10C again allows bone fusion in an angular fashion but this time there is an axial shortening of bellows 14C simultaneous with an angular shape change. Prior to its shape change, fastener 10C looks identical to the first embodiment (fastener 10 as shown in FIG. 2A). The difference is shown in FIG. 7B, wherein fastener 10C is originally manufactured in its austenite, resting, or unstressed phase with a bend in bellows 14C. The end faces 22A and 22B are angled towards each other at pre-determined angles, say anywhere from five degrees to fifty degrees, or from one degree to 60 degrees, or within the other angle ranges as discussed above in regard to the second embodiment. Fastener 10c is manufactured in its austenite phase, as shown in FIG. 7B, and bellows 14C subtends angle $\beta$ which imparts an angle $\alpha$ to the long axis of fastener 10C. Angle $\alpha$ equals angle $\beta$.

After the fastener 10C is manufactured, it is cooled from its austenite to martensite phase to allow its shape to be changed by deformation. The barbs are pressed flat so that they are flush and in alignment with the walls of sleeves 18A and 18B. The fastener is then stretched or elongated and angles $\alpha$ and $\beta$ are eliminated so that the fastener is now linear and not angular. The shape is stable as long as it remains in its martensite phase. When the martensitic phase of the fastener 10C of FIG. 7A is implanted into the body and brought to body temperature, the fastener will deform back to its original austenitic shape of FIG. 7B, thereby shortening along the length of bellows 14C. It will also bend through angle $\alpha$ along the length of the bellows so that the bones of the phalanx can be compressed and fused at the resulting angle $\beta$.

Operation of Third Embodiment

The joint surfaces are prepared as before for the second embodiment. Proximal phalanx 42 and middle phalanx 46 are surgically prepared as before as shown in FIG. 6B. Here abutment surface 78 of proximal phalanx 42 and abutment surface 74 of middle phalanx 46 are prepared so they are at an angle to the long axis of each phalanx respectively. If the surgeon or user wants to fuse the two bones at ten degrees, for instance, then the cut surfaces must be prepared so that the angle formed between the long axes of proximal phalanx 42 and middle phalanx 46 equals ten degrees when both cut surfaces are placed end to end. For example, one surface could be cut at zero degrees or perpendicular to the long axis of the phalanx while the surface of the other phalanx is cut at ten degrees. Alternatively, both phalanges could be cut equally at five degrees. The surgeon will need to choose the implant that is designed to bend ten degrees.

If the surgeon wants to fuse the two bones at fifteen degrees, then she or he would have to prepare the cut surfaces to equal fifteen degrees total angulation. For example, one surface could be cut at zero degrees or perpendicular to the long axis of the phalanx while the surface of the other phalanx is cut at fifteen degrees. Alternatively, both phalanges could be cut equally at seven and one-half degrees and the surgeon would need to use an implant designed to bend fifteen degrees.

After the respective cut surfaces are prepared, each phalanx is then counter-bored preferably to equal depths as in the first embodiment and the implant is then inserted into each phalanx as previously described. The middle and proximal phalanx are then manually held pressed together while fastener 10C goes through its shape change. Herein again barbs 26 deploy and expand outward, being embedded into the surrounding bone. Bellows 14C also goes through its shape change and shortens axially to draw the cut faces of the middle and proximal phalanx toward each other and to bring and compress together these surfaces of the proximal and middle phalanx. Simultaneously, bellows 14C bends along the length of the bellows positioning the phalanxes in an angled arrangement.

Fourth Embodiment

Figure 8A:
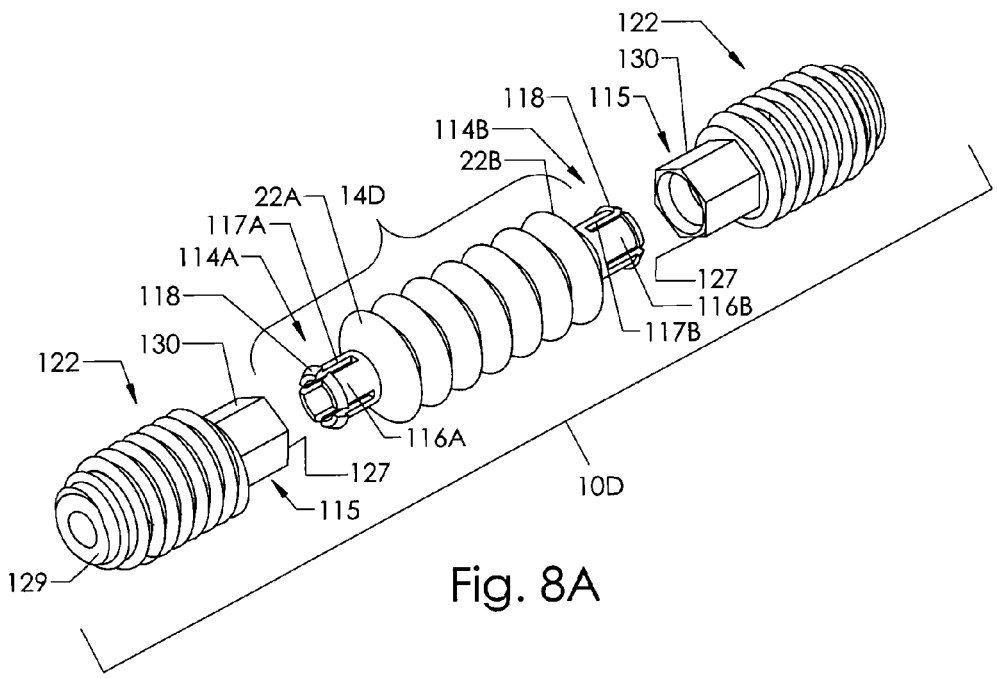
FIG. 8A is a perspective view of an embodiment of the fastener having three separate component parts. There is a central bellows for undergoing a shape change and which is attachable to two identical screws that can be implanted into bones prior to coupling the bellows to these screws. One screw is designated to attach to one side of the bellows while the second screw attaches to the opposite side of the bellows.
Figure 8B:
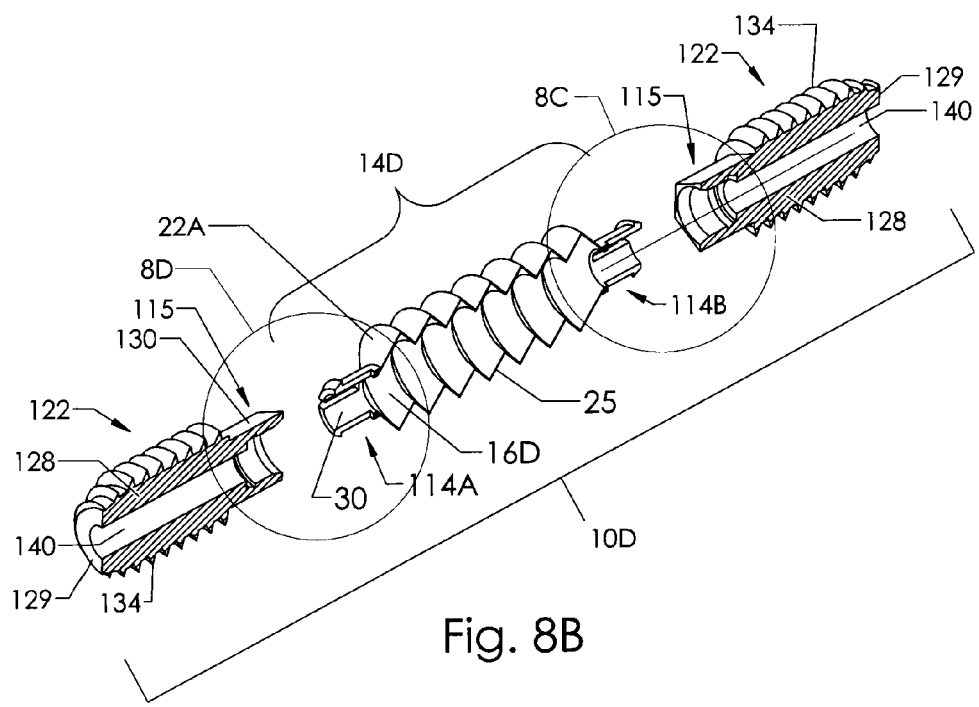
FIG. 8B is a perspective cut-away view of FIG. 8A showing the inside of the fastener of FIG. 8A.
Figure 8C:
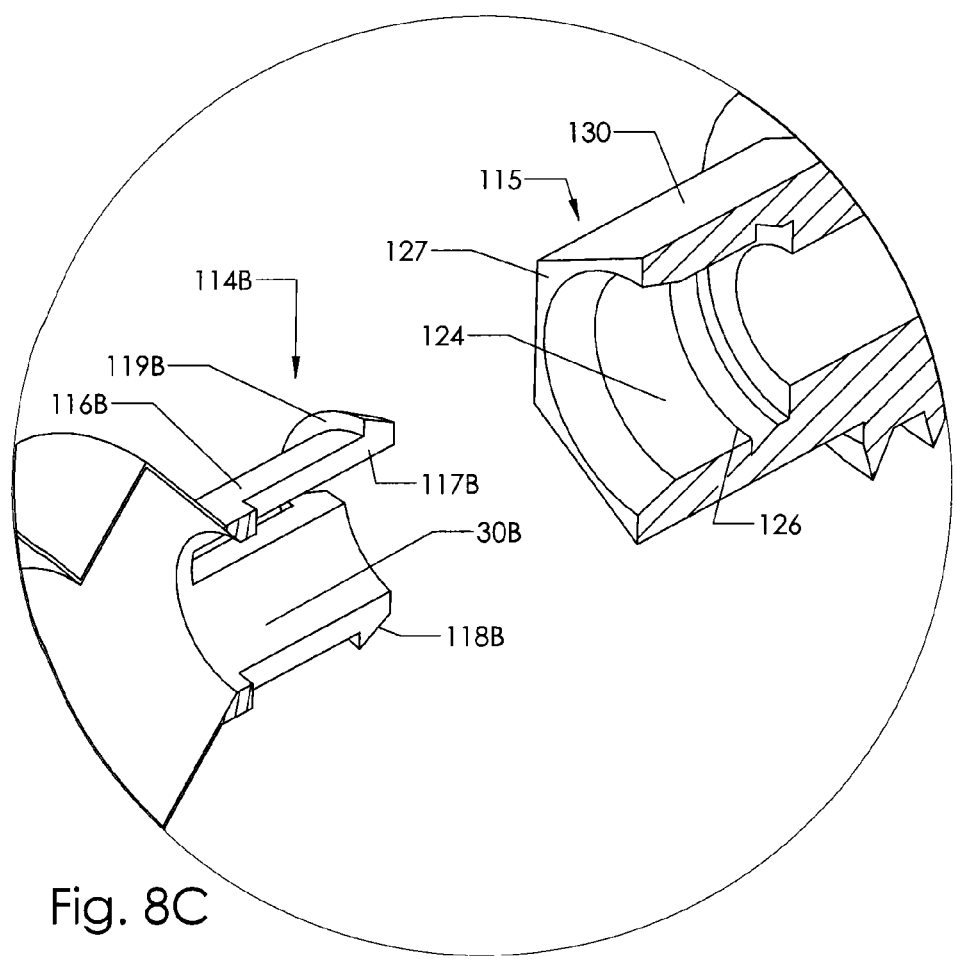
FIG. 8C is an enlarged perspective and cut-away view showing details of the coupling mechanism for joining one end of the bellows to the proximal end of one of the screws of FIG. 8B.
Figure 8D:
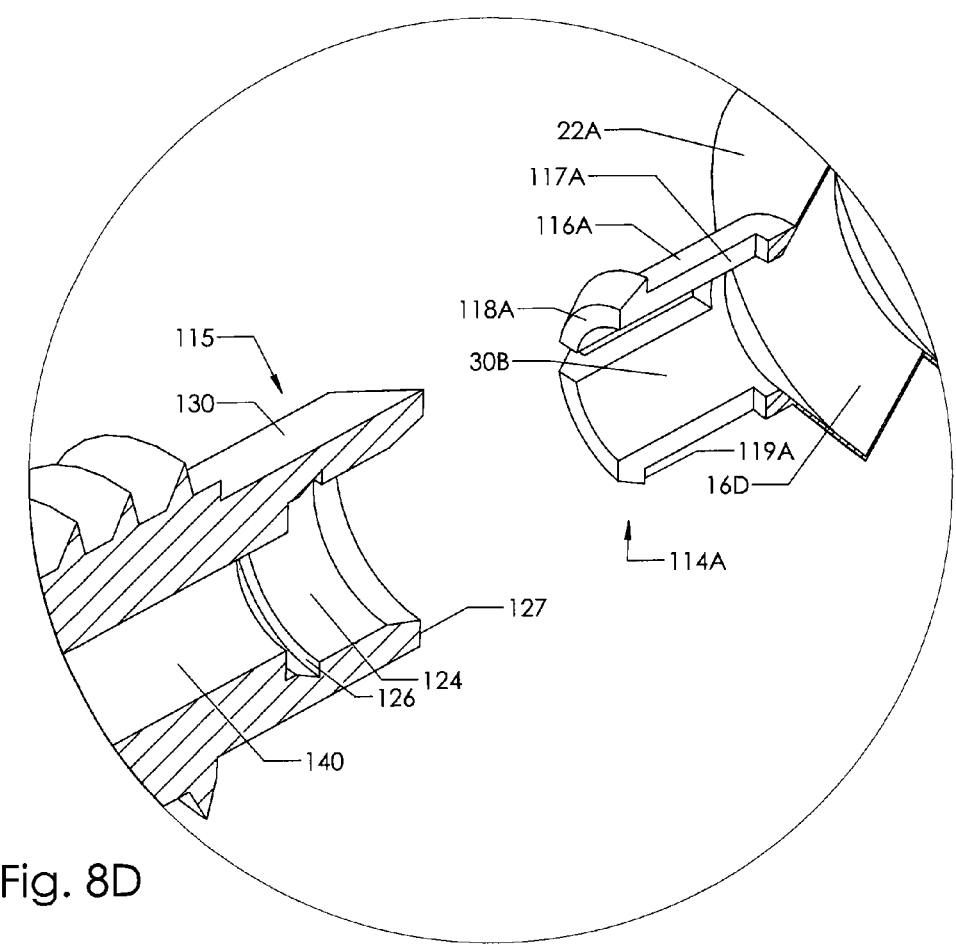
FIG. 8D is an enlarged perspective and cut-away view showing details of the coupling mechanism for joining the other end of the bellows to the proximal end of the other screw of FIG. 8B.

A fourth embodiment includes some substantial differences relative to the above three embodiments with the same end result. FIGS. 8A through 8F shows fastener 10D. Bellows 14D has again an end face 22A and end face 22B. Extending outward in an axial direction from end face 22A and 22B are male connectors or couplers 114A and 114B. Passing axially down the center axis of fastener 10C through male connectors 114A and 114B is cannulation 30 to again accommodate guide wire 34. Hereinafter, the description of male connector 114A will be inclusive of male connector 114B since they are otherwise identical. As best shown in FIGS. 8B and 8D, male connector 114A is formed as a hollow cylindrical tube or sleeve 116A to extend axially from end face 22A of bellows 14D. Sleeve 116A includes an integral ring 118A formed around its end that is opposite to its attachment to end face 22A. Ring 118A extends radially outward from the outer diameter of sleeve 116A and forms a collar 119A, as seen best in FIG. 8D. A collar 119B is formed by a ring 118B on sleeve 116B, which also includes a cannulation 30B, and is easier to see in FIG. 8C.

The sleeve 116A has two cross-cuts along its length to form four slots 117A passing through and extending from ring 118A along sleeve 116A a substantial distance towards end face 22A. Four sections of a spring collet are thus formed out of male connector 114A wherein the sections of the collet can be compressed together towards the center axis of sleeve 118A and will spring back to their original position with removal of the compressive force. Male connector 114A can then be used to couple bellows 14D to a female connector or coupling 115 integrally formed as the proximate end portion of a threaded anchoring member 122, as best seen in FIGS. 8A and 8B. Anchoring member 122 is used twice in this embodiment and for the operation of the embodiment one of the members 122, 122 is positioned at each end of bellows 14D. Anchoring members 122, 122 may be made from shape memory metal though it is not absolutely necessary because they need not undergo any change in its shape. Therefore they may be made from a material that is compatible with the shape memory alloy to avoid any corrosion and should also be biocompatible for implantation into a human or animal body. For instance, if bellows 14D is made from a nickel-titanium shape memory alloy, then members 122, 122 may be of titanium and therein fit the aforementioned criteria. Members 122, 122 could also be made from a biocompatible polymer that may or may not be bioabsorbable.

As shown best in FIGS. 8A and 8B, each member 122 has a cylindrical body 128 and its female connector 115 has an end face 127. Male connector 114B is used to couple bellows 14D to the second member 122 by engaging its female connector or coupling 115 integrally formed as its proximate end portion as best seen in FIG. 8C. A central longitudinal cylindrical cavity 124, as seen best in FIGS. 8C and 8D, extends longitudinally into body 128 of members 122, 122 through the end face 127. Passing axially through body 128 is a cannulation 140 to allow passage of guide wire 34. Cavity 124 has an internal diameter and length to accommodate male connectors 114A and 114B. To allow for coupling to occur, cavity 124 has a circular recess 126 set radially around its inner wall. It is positioned and extends substantially along the circumference of the wall of the cavity opposite end face 127. Collars 119A and 119B of rings 118A and 118B, respectively, will snap into recesses 126, 126 when male connectors 114A and 114B are inserted forcefully into cavities 124, 124. Upon insertion of male connectors 114A, 114B into cavities 124, 124, the internal wall of these cavities will maintain the sections of the spring collets compressed together until collars 119A, 119B reach recesses 126, 126. Thereat, rings 118A, 118B seat themselves into recesses 126, 126 locking together the bellows 14D and the two threaded members 122, 122.

Bellows 14D and male connectors 114A and 114B are generally all made from the shape memory metal, although the male connectors themselves are not cold deformed and therefore do not undergo a shape memory change. There is motion across the male connectors when the spring collet is compressed by the internal diameter of anchoring member 122 but this is due to force applied on the spring collet and not action of the shape memory metal. However, collars 119A and 119B could be designed to change shape. For example, the collar could be designed such that in the austenite phase, the collar is angled or bent axially in the direction of bellows 14D. In the martensite phase, the collar would be in a position where it is angled axially away from the bellows. Then, upon implantation into the body and warming of the metal, phase change from martensitic back to austenitic would cause collars 119A and 119B to change its shape. This would cause the collars to bend or angle back toward their original positions, directed substantially in the direction of the bellows. When bellows 14D is coupled to member 122, the phase change in the collar would help to further pull together the two devices, adding to the compression provided by the fastener.

Figure 8E:
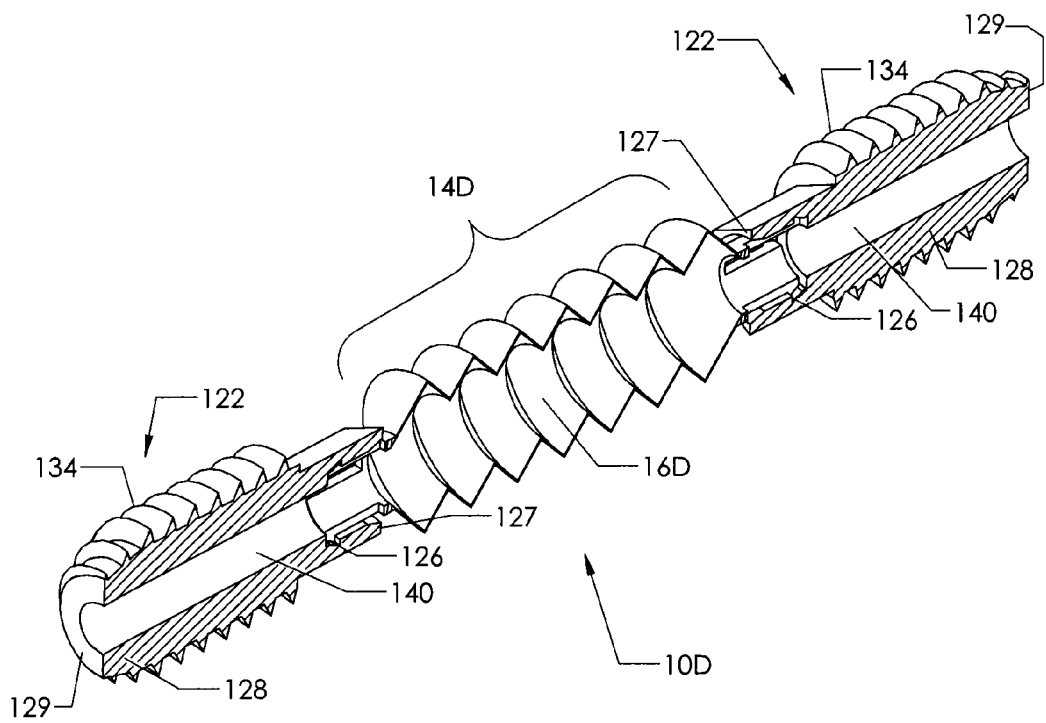
FIG. 8E is a perspective cut away view showing an alternative embodiment of the fastener in its martensitic phase with each end of the bellows joined to a screw.
Figure 8F:
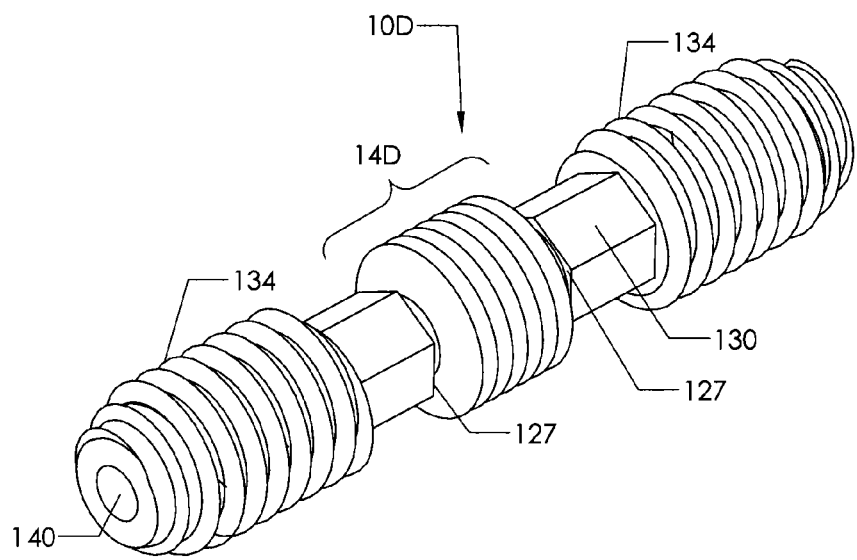
FIG. 8F is a perspective view of the alternative embodiment of FIG. 8F showing the bellows in its austenitic shortened phase with each end of the bellows joined to a screw.

When anchoring members 122, 122 and bellows 14D are coupled together, cannulations 140, 140 are axially aligned with the bellows chamber 16D as shown best in FIGS. 8B and 8E. FIGS. 8A, 8C, and 8F show that at the end of member 122 adjacent to end face 127, there extends along the female coupling portion of body 128 in a direction opposite to end face 127 a tool receiving surface 130 for engagement by a tool such as a screw driver having a correspondingly shaped receptacle or cannulation. The outer perimeter of surface 130 has a hexagonal cross-sectional shape in this embodiment, although square, torn or cruciate cross sectional shapes would also be acceptable as these are other common shapes for screwdrivers available in an operating room. In this embodiment with the hexagonal shaped tool surface 130, a screwdriver (not shown) with a hexagonal receptacle may be slid over surface 130 for the purposes of turning member 122 axially into a bone. Member 122 includes a thread or plurality of threads 134 formed around a body 128 and extending the length of body 128 from the inner end of the surface 130 opposite end face 127 to the end face 129 at the opposite end of body 128. These threads are for anchoring member 122 into a middle or proximal phalanx. As stated earlier, member 122 does not go through a shape change and therefore does not necessarily need to be made from a shape memory metal.

However, member 122 can be made from a shape memory metal which would allow some modifications of the anchoring method into bone. For instance, instead of body 128 having threads 134, the body could have barbs, similar to the prior embodiments, that expand when implanted into a proximal or middle phalanx or other substrate. Male connector 114A of bellows 14D would then be inserted into cavity 124 and coupled with member 122, effectively achieving the same goal. Other anchoring methods could be used as well. Two different types of screws could be used or two members that are only differentiated by the thread patterns going in opposite directions. One screw would be screwed into the bone clockwise, the other counterclockwise. Furthermore, as alternatives to these designs, bellows 14D can be made in a similar angular manner as that shown for bellows 14B in FIG. 6A or bellows 14C of FIG. 7B.

Other coupling arrangements besides the spring collet design could also be used to join together anchoring members 122, 122 and bellows 14D. A strike-and-latch type coupling mechanism or push-lock mechanism could be employed in the design as well for any of the embodiments hereinafter described. Also, although the male couplings 114A and 114B and the female couplings 115, 115 are not designed to be detachable after being joined, other coupling arrangements designed to be detachable after joinder are well known in the coupling art. In addition, the coupling mechanisms of other coupling arrangements could have shape memory capabilities as described above for the collars 119A and 119B on the spring collets of this embodiment.

Operation of Fourth Embodiment

As seen in FIGS. 5A and 5B, the joint surfaces of proximal phalanx 42 and middle phalanx 46 are again prepared as previously described for the first embodiment. The cut surfaces 78 and 74 are prepared so that their surfaces are perpendicular to the long axis of the bones. Herein again guide wire 34 is driven axially into proximal phalanx 42 using wire driver 38. A counter-borer, as in the first embodiment in FIG. 5C, that matches the thread root diameter of member body 128 is placed over guide wire 34 and used to make matching bore holes in proximal phalanx 42 and middle phalanx 46. The counter-borer is removed from the guide wire. Member 122 is then placed over guide wire 34 followed by a screwdriver (not shown) having a hexagonal shaped cannulation. This screwdriver is then mated with tool surface 130, shown best in FIG. 8A, and then member 122 is screwed into proximal phalanx 42 to appropriate depth. A similar procedure is then performed on middle phalanx 46 and a second member 122 is screwed into middle phalanx 46.

Refrigerated bellows 14D is now manually implanted into the proximal phalanx 42 and the middle phalanx 46 per the following. Male connector 114A, again shown best in FIGS. 8A and 8D, is pushed into cavity 124. The spring collet is compressed by the walls of cavity 124 until collar 119A of ring 118A slips into recess 126, locking male connector 114A and bellows 14D to member 122. Proximal phalanx 42 and middle phalanx 46 are grasped by the surgeon's hands, just as in the main embodiment, and male connector 114B is manually inserted into cavity 124 of the second member 122 in middle phalanx 46. Again collar 119B of ring 118B snaps into recess 126 locking together bellows 14D and the second member 122. At this point, bellows 14D is connected on both its ends to a member 122 in proximal phalanx 42 and a member 122 in middle phalanx 46. FIG. 8F shows fastener 10D as assembled with bellows 14D situated between the two anchoring members 122 and coupled together with them. The fastener is shown here in its austenite phase with bellows 14D contracted and shortened.

Figure 9:
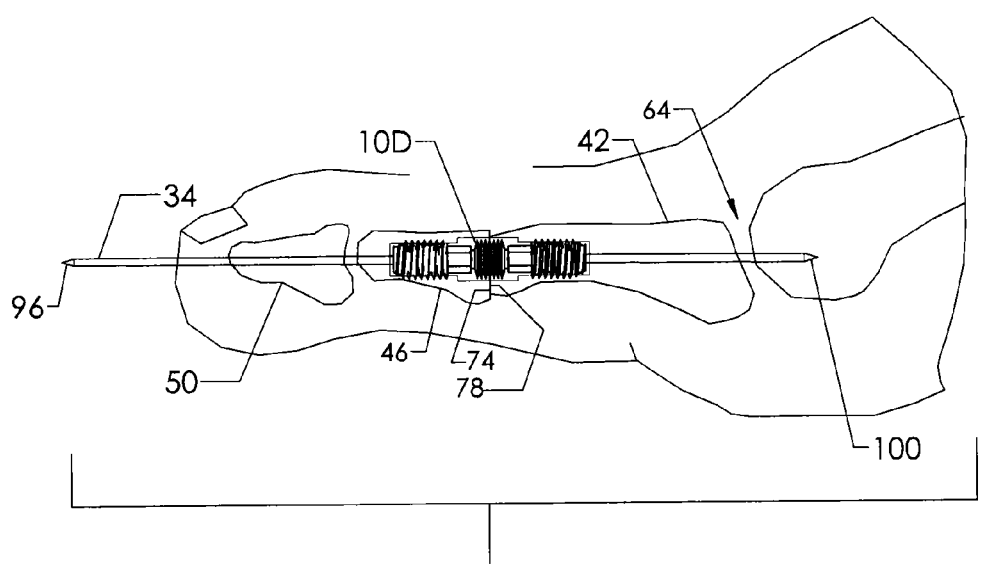
FIG. 9 is a side elevation view of the alternative embodiment of FIG. 8F showing the fastener implanted into a proximal interphalangeal joint. The bellows is in its austenitic shortened phase with a guide wire implanted through the toe and into the metatarsal, passing through the cannulation of the fastener.

As the temperature of shape memory bellows 14D increases to body temperature, it undergoes a change in shape from its annealed elongated martensite phase to its shortened austenite phase, drawing together surface 78 of proximal phalanx 42 and surface 72 of middle phalanx 46. FIG. 9 shows fastener 10D implanted into a PIPJ and in its austenite phase. After the two surfaces become compressed, the surgeon may then decide whether he or she needs to place proximal end 100 of guide wire 34 across MTPJ 64, and leave it within fastener 10D, or remove guide wire 34 entirely from the fastener and the toe. Wire driver 38 is used to place the guide wire in the appropriate position. After removal of the guide wire, the surgeon then closes the wound utilizing a standard surgical technique.

Fifth Embodiment

Figure 10:
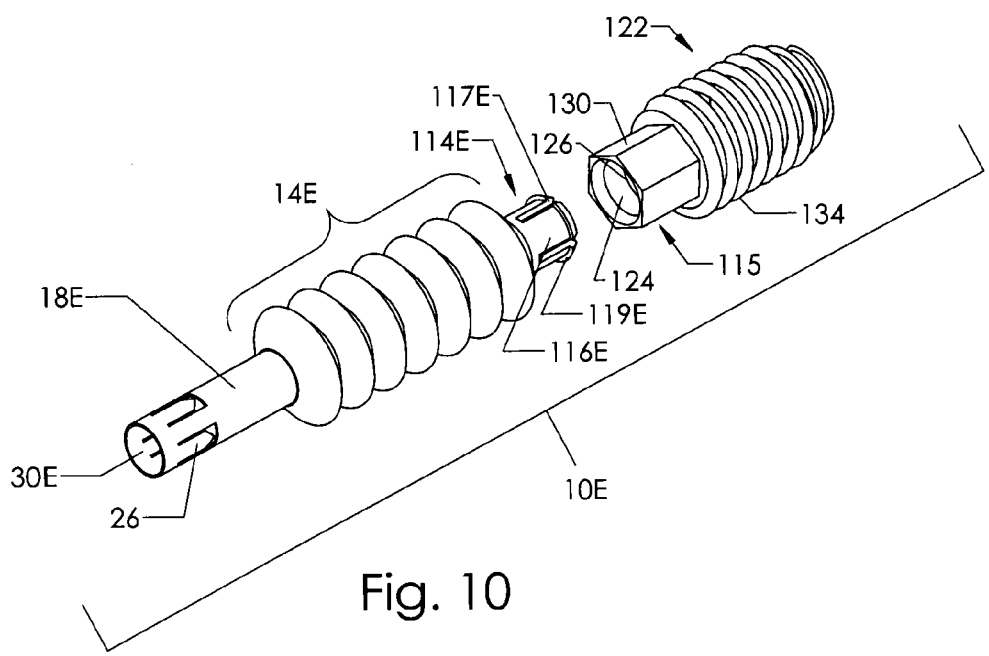
FIG. 10 is an exploded perspective view of an alternative embodiment of the fastener showing two separated component parts of the embodiment. There is a central bellows and one end of the bellows has an integral sleeve with barbs for fastening into bone. The other end of the bellows has a coupling mechanism for attaching to a screw for implanting into another bone.

Another alternative embodiment is shown in FIG. 10 wherein the embodiment shows combinations of components of the previous embodiments. Here, fastener 10E has a sleeve 18E which extends axially outward from bellows 14E. Again barbs 26 are substantially positioned outward from the bellows along the length of sleeve 18E. At the end of bellows 14E opposite the sleeve 18E extending axially is a male connector 114E. Cannulation 30E passes along the internal central axis of the sleeve and bellows. A member 122 is the same as described in the fourth embodiment. Member 122 may be made from a shape memory metal alloy, shape memory polymer, or other biocompatible alloy or polymer.

Male connector 114E has similar design and makeup as male connectors 114A and 114B from the fourth embodiment. Male connector 114E has two cross-cuts 117E down its length to form four sections of a spring collet. At the end of male connector 114E is collar 119E which engages the internal diameter of member 122 as described for the fourth embodiment. The collar may have shape memory action as previously described or may be made without it and the collar and the entire male connector may or may not be made from shape memory materials. The action of the male connector is likewise the same as previously described for the fourth embodiment. Here again the coupling mechanism of this embodiment need not be based on a spring collet design. A strike and latch mechanism or a push-lock mechanism, either one with or without shape memory action, could be employed to achieve coupling of screw member 122 to bellows 14E of the fastener 10E. Also, as shown in prior embodiments, the present embodiment and all others to follow may be angular in design to allow a joint to be fused in a position other than straight.

Operation of Fifth Embodiment

In using fastener 10E, the bones of a toe are prepared as previously described in FIGS. 5A and 5B. Here again a guide wire 34 is driven axially into proximal phalanx 42 using a wire driver 38. A counter-borer, as in the first embodiment in FIG. 5C, that matches the thread root diameter of member body 122 is placed over guide wire 34 and used to make a bore hole 110 in proximal phalanx 42. The counter-borer is removed from the guide wire. Member 122 is then placed over guide wire 34 followed by a screwdriver having a hexagonal shaped cannulation to fit over the tool surface 130 of member 122. This screwdriver is then mated with tool surface 130 and then member 122 is screwed into proximal phalanx 42 to appropriate depth. Next the guide wire is placed into middle phalanx 46 and a counter-borer is used to create a matching bore hole 111 in abutment surface 74 of the middle phalanx.

Refrigerated bellows 14E is now manually implanted into the proximal phalanx 42. Male connector 114E is pushed into cavity 124 of member 122. The spring collet is compressed by the walls of cavity 124 until collar 119E slips into recess 126 of member 122, locking male connector 114E and bellows 14E to member 122. Proximal phalanx 42 and middle phalanx 46 are grasped by the surgeon's hands, just as in the main embodiment, and sleeve 18E of the fastener is slid into matching bore hole 111 in middle phalanx 46. The two abutment surfaces are brought together and the bellows is warmed by body heat. This allows the bellows and the barbs to change shape. The barbs expand radially outward into the surrounding bone and the bellows contracts axially to compress the abutment surfaces together.

Sixth Embodiment

Figure 11:
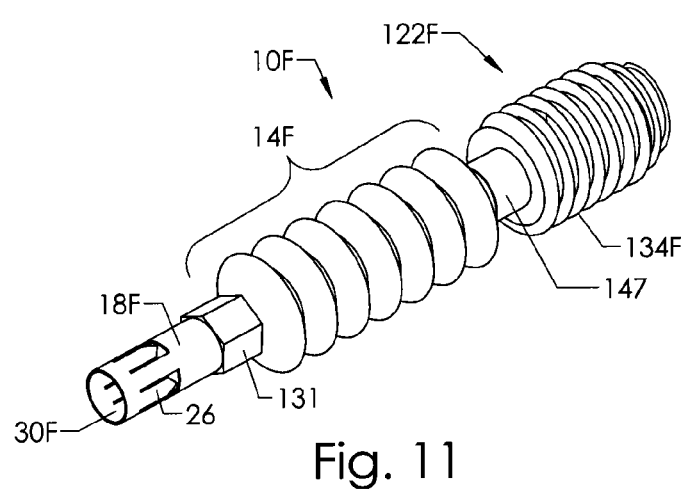
FIG. 11 is a perspective view of an alternative embodiment showing a single piece construct with integral sleeves. The central bellows has an integral screw at one end as a means for implanting and securing the fastener into bone and the opposite end has an integral sleeve with barbs for anchoring the fastener into another bone.

FIG. 11 shows another embodiment where again there is a single construct for implantation into bone. A fastener 1 OF is shown having components of the previous embodiments. A bellows 14F is again noted centrally along the axis of fastener 10F. Extending axially outward away from bellows 14F is again an integral sleeve 18F with barbs 26. Extending axially outward away from bellows 14F opposite sleeve 18F is screw member 122F. Member 122F has threads 134F extending inward from its end substantially toward bellows 14F. In this embodiment, however, screw member 122F is attached to bellows 14F either directly or via a small arm 147 situated between the bellows and body. Again, sleeve 18F, bellows 14F, arm 147, and body 122F are all generally axially aligned and there is a longitudinal central cannulation 30F to the entire fastener as noted in the first embodiment. Situated substantially opposite barbs 26 and adjacent bellows 14F, sleeve 18F is modified into a tool surface 131. Tool surface 131 is generally hexagonal shaped to allow a hex screwdriver to slide over sleeve 18F and engage the tool surface. A screwdriver may then be used to turn the entire fastener 10F to first drive screw member 122F into a bone.

Being a single construct, the entire fastener 10F is preferably made of a shape memory alloy though it is still possible that screw member 122F could be made of a non-shape memory metal like titanium. The screw part and the bellows part could be integral or instead made independently and then welded together to form a single construct. Again, this embodiment may also be made angularly instead of straight as set forth in prior embodiments. Conceivably the sleeve end of fastener 10F could be made as a separate piece from bellows 14F. A coupling arrangement as previously described, say a spring collet mechanism, a push-lock mechanism or a strike and latch mechanism, could then be used as a way of joining together the barbed sleeve 18F and bellows 14F with its attached screw member 122F after both segments of the embodiment have been separately implanted into the bones to be fused.

As with embodiments one to five above, an angularity could be imparted to this sixth embodiment so that the bones to be fused are set at an angle to one another. Also, the entire construct need not necessarily be entirely made up of shape memory metal or polymer as long as the parts of the embodiment needing to undergo a shape change are made of shape memory material. As previously indicated, when the fasteners described above change shape from an extended state to a contracted state upon being heated, they are considered to be heat responsive and may be referred to as heat responsive fasteners.

Operation of Sixth Embodiment

In using fastener 10F, the bones of a toe are prepared as previously described in FIGS. 5A and 5B. Here again a guide wire 34 is driven axially into proximal phalanx 42 using a wire driver 38. The counter-borer matches the thread root diameter of member body 122F. It is placed over guide wire 34 and used to make a bore hole 110 in proximal phalanx 42. The counter-borer is removed from the guide wire. Fastener 10F is then placed over guide wire 34 followed by a screwdriver having a hexagonal shaped cannulation to fit over the tool surface 131 of fastener 10F. This screwdriver is then mated with tool surface 131 and the entire fastener 10F, not just body 122F, is screwed into proximal phalanx 42 to appropriate depth. Next the guide wire is removed and placed into middle phalanx 46 and a counter-borer is used to create a matching bore hole 111 in abutment surface 74 of the middle phalanx that will match the half of fastener 1 OF that encompasses sleeve 18F and barbs 26. Proximal phalanx 42 and middle phalanx 46 are grasped by the surgeon's hands, just as in the main embodiment, and sleeve 18F of the fastener is slid into matching bore hole 111 in middle phalanx 46. The two abutment surfaces are brought together and the bellows is warmed by body heat. This allows the bellows and the barbs to change shape. The barbs expand radially outward into the surrounding bone and the bellows contracts axially to compress the abutment surfaces together.

Seventh Embodiment

Figure 12:
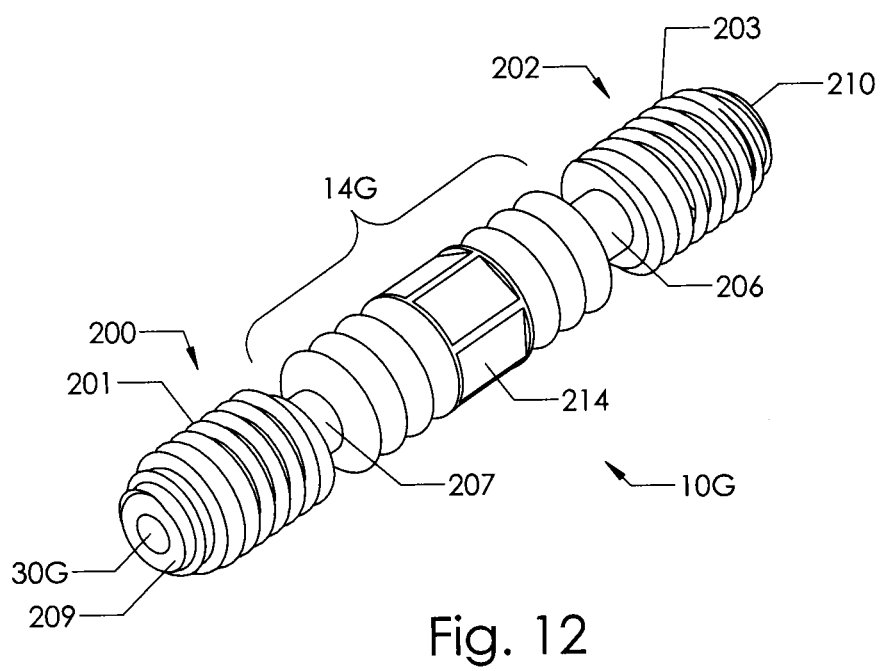
FIG. 12 is a perspective view of an alternative embodiment of the fastener showing a single piece construct wherein the central bellows portion of the fastener is integrally connected at each end to a screw. One screw has right hand turning threads while the other screw has left hand turning threads.

FIG. 12 shows an embodiment similar in appearance to the fourth embodiment. The most notable difference in a fastener 10G are integral screws 200 and 202 solidly attached to each end of a bellows 14G wherein screws 200 and 202 have oppositely handed thread patterns to each other. Screw 200 has an end face 209 set on the end of the screw opposite the direction of the centrally positioned bellows 14G. A set of threads 201 extending inwardly from end face 209 surrounds the periphery of screw 200. Threads 201 are left hand turning in their operation. A set of threads 203 extending inwardly from an end face 210 surrounds the periphery of screw 202. Threads 202 are right hand turning in their operation. An arm 207 connects screw 200 to bellows 14G whereas an arm 206 connects screw 202 to bellows 14G. Screw 200, arm 207, bellows 14G, arm 206, and screw 202 are all axially aligned.

Fastener 10G has a cannulation 300 running centrally down the long axis of the fastener for passage of a guide wire as in prior embodiments. The cannulation extends from end face 209 of screw 200 to end face 210 of screw 202. The circumference of the central pleat of bellows 14G is modified into a hexagonal shaped tool surface 214, or hex nut, dividing the bellows in half. Each half of the bellows is integrally connected to each side of the hex shaped tool surface 214.

Bellows 14G is again preferably made entirely of a shape memory material but those parts that do not undergo shape change do not necessarily need to be. Since the tool surface 214 does not undergo a change in its shape, it could be made from an alternative biocompatible alloy or metal and the two halves of the bellows may be welded to it. Screws 200 and 202 also could be made from a metal or alloy other than a shape memory alloy since this portion of the embodiment also need not undergo a shape change. These too could be welded to the bellows directly or via arms 207 and 206. As with the previously described embodiments, when the bellows changes shape from an extended state to a contracted state upon being heated, the fastener is considered to be heat responsive and may be referred to as a heat responsive fastener.

Though FIG. 12 represents an embodiment where screws 200 and 202 are solidly attached, conceivably a mechanism could be used for detachably coupling the screws to the bellows. Here a strike and latch coupling mechanism may be appropriate or some similar design such that the coupling mechanism permits the transfer of torque to screws 200 and 202, described below in the operation of fastener 10G. If the screws are not integral to the bellows, then they could be made from a biocompatible polymer which could again be detachably coupled to the bellows 14G.

Operation of Seventh Embodiment

Placing the embodiment across the PIPJ for joint fusion is not unlike the prior embodiments. The joint surfaces are again prepared as before. A guide wire and counter-borer are again used in the proximal phalanx and a matching bore hole is made. Again, one end of fastener 10G is slid over the guide wire in the proximal phalanx and placed inside the phalanx. The guide wire is then removed and directed into the middle phalanx and out the end of the toe. A matching bore hole is then made in the middle phalanx. The middle phalanx is then slid over the other end of the fastener and the guide wire allowed to slide down cannulation 30G. Once the fastener is in position spanning the joint space, the design and operation of the embodiment is such that the hexagonal tool surface is centrally aligned over the joint space with the screws and bellows inside the bones. There is some space or gapping between the abutment surfaces of the proximal and middle phalanx. A hex shaped wrench is then placed over the hex tool surface 214 and used to turn the fastener. This transmits torque to screws 200 and 202 such that, coupled with the action of the left and right hand screws, turning the fastener in only one direction drives both of the screws into the respective bones thereby embedding them therein and anchoring them into the phalanges. This then draws the proximal and middle phalanx closer together. The hex wrench is then removed and the shape change of bellows 14G, upon warming up, completes the process of compressing together the abutment surfaces of the proximal and middle phalanx. Subsequently the surgeon may then decide whether to drive the guide wire across the MTPJ, leave it where it is, or remove it altogether prior to closure of the surgical wound.

What is claimed is:

1. A bellows fastener for joining together two separate pieces, said fastener comprising:
    a bellows comprising a material that changes shape when activated by a catalyst, and having a structure causing said bellows to contract from an extended state to a contracted state when said shape changing material is activated by said catalyst so that a first side of the bellows moves toward a second side thereof;
    a first sleeve having a first proximate end with first means for connecting said first proximate end to the first side of said bellows, and a first distal end with first anchoring means for attaching said first distal end to one of said pieces; and,
    a second sleeve having a second proximate end with second means for connecting said second proximate end to the second side of said bellows, and a second distal end with second anchoring means for attaching said second distal end to the other of said pieces;
    wherein said first and second connection means connect said first and second proximate ends respectively to said first and second sides of the bellows so that activation of said bellows by said catalyst while the bellows is in its extended state causes said bellows to contract and its first and second sides to pull said first and second sleeves and their distal ends toward each other.

2. A bellows fastener according to claim 1, wherein the shape changing material is activated by a change in temperature, wherein said bellows has a cool state corresponding to said extended state and a warm state corresponding to said contracted state, and wherein said bellows has a structure causing said bellows to shorten axially when heated from said cool state to said warm state.

3. A bellows fastener according to claim 2, wherein at least one of said anchoring means comprises one or more barbs made of a material that changes shape when activated by a change in temperature, and has a structure causing said one or more barbs to expand outwardly for engaging a bore in a corresponding one of said pieces when implanted therein and said shape changing material is heated to a warm state from a cool state.

4. A bellows fastener according to claim 1, wherein each of said sleeves has a central cannulation and said bellows has a central chamber, said cannulation and said chamber being sized and aligned so as to receive a guide wire for guiding the distal end of each of said sleeves into an imbedded position within a corresponding one of said pieces, and said sleeves and said bellows being arranged so that said guide wire may remain in place after the distal ends of said sleeves are in their imbedded positions.

5. A bellows fastener according to claim 1, wherein the first side of said bellows comprises a face in a plane normal to a central axis of a first portion of said bellows, wherein the second side of said bellows comprises a face in a plane normal to a central axis of a second portion of said bellows, wherein said bellows further comprises an integral collar connected between said first and second bellows portions and having an asymmetrical structure causing said faces to be at an angle relative to each other such that the respective central axes of said bellows portions intersect at a corresponding angle, and wherein said first sleeve has a central axis aligned with the central axis of said first bellows portion and said second sleeve has a central axis aligned with the central axis of said second bellows portion.

6. A bellows fastener according to claim 1, wherein at least one of said anchoring means comprises one or more barbs made of a material that changes shape when activated by a catalyst, and has a structure causing said barbs to expand outwardly for engaging a bore in a corresponding one of said pieces when implanted therein and said shape changing material is activated.

7. A bellows fastener according to claim 1, wherein at least one of said anchoring means comprises external threads extending inwardly along an end portion of the sleeve adjacent the distal end thereof.

8. A bellows fastener according to claim 1, wherein one of said anchoring means comprises a screw segment having external threads extending inwardly along an end portion of the sleeve adjacent the distal end thereof; and wherein the other of said anchoring means comprises a barb segment of the sleeve having one or more barbs made of a material that changes shape when activated by a change in temperature, and has a structure causing said one or more barbs to expand outwardly for engaging a bore in a corresponding one of said pieces when implanted therein and said shape changing material is heated to a warm state from a cool state.

9. A bellows fastener according to claim 8, wherein the proximate end of the sleeve with the barb segment is integrally connected to said bellows, and the proximate end of the sleeve with the screw segment comprises coupling means for connecting said screw segment sleeve to said bellows.

10. A bellows fastener according to claim 1, wherein each of said anchoring means comprises a screw segment having external threads extending inwardly along an end portion of the corresponding sleeve adjacent the distal end thereof, wherein said sleeves are integrally connected to said bellows, and wherein the threads of one of said screw segments are right-handed and the threads of the other of said screw segments are left-handed, said right-handed threads being slanted in a direction opposite to said left-handed threads such that the turning of said fastener in a single direction when said threads are engaged with corresponding bores in said pieces causes said pieces to be pulled together.

11. A bellows fastener according to claim 1, wherein said sleeves and said bellows are separate elements, and wherein said fastener further comprises a first coupling means for connecting the proximate end of said first sleeve to the first side of said bellows, and a second coupling means for connecting the proximate end of said second sleeve to the second side of said bellows.

12. A bellows fastener according to claim 1, wherein said bellows and at least one of said sleeves are separate elements, and wherein said fastener further comprises a coupling means for connecting the proximate end of said separate sleeve to one of the sides of said bellows.

13. A bellows fastener according to claim 1, wherein said shape changing material is a metal alloy or a polymer.

14. A bellows fastener according to claim 1, wherein at least a portion of at least one of said sleeves is made of a shape changing material.

15. A bellows fastener according to claim 5, wherein at least a portion of said collar is not made of a shape changing material.

16. A method of using the bellows fastener of claim 1 for joining together a first piece separate from a second piece, said method comprising:
providing respective contact surfaces on said first and second pieces;
providing a first bore in said first piece at or adjacent to the contact surface thereof, and a second bore in said second piece at or adjacent to the contact surface thereof;
inserting the anchoring means of said first sleeve into said first bore, and inserting the anchoring means of said second sleeve into said second bore;
causing said first anchoring means to engage a wall of said first bore to fix said first sleeve therein, and causing said second anchoring means to engage a wall of said second bore to fix said second sleeve therein; and,
activating said shape changing material with said catalyst to cause said separate pieces to be pulled together by said bellows such that the respective contact surfaces thereof are brought into abutment and compressed against each other.

17. A method according to claim 16, wherein each of said anchoring means comprises a barb segment having one or more barbs made of a material that changes shape when activated by said catalyst and has a structure causing said barbs when activated to expand outwardly and engage the wall of the corresponding bore into which the anchoring means has been inserted.

18. A method of treating a hammertoe condition of a foot using the bellows fastener of claim 2, said method comprising:
separating a middle phalanx from a proximal phalanx at an interphalangeal joint between opposing ends of said middle and proximal phalanxes;
providing substantially flat contact surfaces by removing bone tissue from said ends after separation of said middle and proximal phalanxes;
providing a first bore in said middle phalanx at the contact surface thereof, and a second bore in said proximal phalanx at the contact surface thereof;
inserting the first anchoring means of said first sleeve into said first bore, and inserting the second anchoring means of said second sleeve into said second bore;
causing said first anchoring means to engage a wall of said first bore to fix said first sleeve therein, and said second anchoring means to engage a wall of said second bore to fix said second sleeve therein; and,
heating said bellows from its cool state to its warm state to cause the contact surfaces of said middle and proximal phalanxes to be pulled together and compressed against each other.

19. A method of treating hammertoe according to claim 18, wherein each of said sleeves has a central cannulation and said bellows has a central chamber, said cannulations and said chamber being sized and aligned so as to receive a guide wire for guiding said first anchoring means into said first bore and said second anchoring means into said second bore; wherein said method further comprises placing said guide wire in a stabilizing position by passing it through a distal phalanx aligned with said middle phalanx, across a distal interphalangeal joint between said distal phalanx and said middle phalanx, through said middle phalanx, across said compressed contact surfaces, and into said proximal phalanx; and wherein said guide wire may remain in said stabilizing position until said compressed contact surfaces heal to form an integral connection between said middle and proximal phalanxes.

20. A method of treating hammertoe according to claim 19, wherein placing said guide wire in said stabilizing position further includes passing it through said proximal phalanx, across a metatarsal-phalangeal joint between said proximal phalanx and an aligned metatarsal, and into an end portion of said metatarsal.

\* \* \* \* \*